(12) United States Patent
Reddy et al.

(10) Patent No.: US 7,354,715 B2
(45) Date of Patent: Apr. 8, 2008

(54) HIGH-THROUGHPUT METHODS OF SCREENING DNA FOR DELETIONS AND OTHER MUTATIONS

(75) Inventors: Avutu Sambi Reddy, Carmel, IN (US); Max Otto Ruegger, Indianapolis, IN (US); James Patrick Connell, Indianapolis, IN (US); Thomas Skokut, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 200 days.

(21) Appl. No.: 10/851,924

(22) Filed: May 21, 2004

(65) Prior Publication Data

US 2005/0053975 A1    Mar. 10, 2005

Related U.S. Application Data

(60) Provisional application No. 60/472,863, filed on May 22, 2003.

(51) Int. Cl.
   *C12Q 1/68*     (2006.01)
   *C07H 21/02*    (2006.01)
   *C07H 21/04*    (2006.01)
(52) U.S. Cl. .................. 435/6; 536/23.1; 536/24.3
(58) Field of Classification Search .............. 435/6, 435/440; 536/23.1, 24.3
   See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,185,244 A * | 2/1993 | Wallace | 435/6 |
| 5,234,811 A * | 8/1993 | Beutler et al. | 235/6 |
| 5,354,670 A * | 10/1994 | Nickoloff et al. | 435/91.53 |
| 5,891,625 A | 4/1999 | Buchardt et al. | |
| 5,994,075 A | 11/1999 | Goodfellow | |
| 6,110,709 A * | 8/2000 | Ausubel et al. | 435/91.2 |
| 6,358,690 B1 | 3/2002 | Krysan et al. | |
| 6,484,105 B2 | 11/2002 | Zhang | |
| 6,514,736 B1 * | 2/2003 | Erlich et al. | 435/194 |
| 2002/0064879 A1 | 5/2002 | Zhang | |
| 2003/0008307 A1 * | 1/2003 | Griffin et al. | 435/6 |
| 2003/0162174 A1 * | 8/2003 | Sutherland | 435/6 |
| 2004/0237134 A1 * | 11/2004 | Pozniak et al. | 800/278 |
| 2006/0134617 A1 * | 6/2006 | Manen et al. | 435/6 |

FOREIGN PATENT DOCUMENTS

| | | |
|---|---|---|
| DE | 197 33 619 C1 | 2/2000 |
| EP | 1 266 970 A2 | 12/2002 |
| WO | WO96/32500 * | 10/1996 |
| WO | WO 98/50539 | 11/1998 |
| WO | WO 99/51774 | 10/1999 |
| WO | WO 00/28081 A2 | 5/2000 |
| WO | WO 01/75167 A1 | 10/2001 |

OTHER PUBLICATIONS

Ballinger et al. Targeted gene mutations in Drosophila. PNAS 86 : 9402-9406 (1989).*
Felley-Bosco et al. A genotypic mutation system measuring mutations in restriction recognition sequences. Nucleic Acids Research 19(11): 2913-2919 (1991).*
Koornneef et al., EMS- and radiation-induced mutation frequencies at individual loci Arabidopsis thaliana (L.) Heynh. Mutation Research 93 :109-123 (1982).*
Kronenberg A., Perspectives on Fat-Neuton Mutagenesis of human lymphoblastoid cells. Radiation Research 128 (1) Suppl.: S87-S93 (1991).*
Parry et al., Restriction site mutation analysis, a proposed methodology for the detection and study of DNA base changes following mutagen exposure. Mutagenesis 5(3) : 209-212 (1990).*
Parsons et al., Genotypic Selection methods for the direct analysis of point mutations. Mutation Research 387 : 97-121 (1997).*
Pourzand et al., Genetic mutation analysis by RFLP/PCR. Mutation Research 288 : 113-121 (1993).*
Ronai et al., Quantitative Enriched PCR (QEPCR), a highly sensitive method for detection of K-ras oncogene mutations. Human Mutation 10 : 322-325 (1997).*
Sandy et al. Genotypic analysis of mutations in Taq I restriction recognition sits by Restriction fragment length polymorphism/polymerase chain reaction. PNAS 89 : 890-894 (1992).*
Wei et al. , Efficient isolation of targeted Caenorhabditis elegans deletion strains using highly thermostable restriction endonucleases and PCR. Nucleic Acids Research 30(20) e110 pp. 1-8 ( Oct. 2002).*
Ballinger, D.G., et al., "Targeted Gene Mutations in Drosophila, " Proc. Natl. Acad. Sci. USA (Dec. 1, 1989) (abstract), vol. 86, No. 23.
Bruggermann, E., et al., "Analysis of fast neutron-generated mutants at the Arabidopsis thaliana HY4 locus," The Plant Journal (1996), p. 755-760. vol. 10, No. 4.
Edgley, M., et al., "Improved detection of small deletions in complex pools of DNA," Nucleic Acids Research (2002), vol. 30, No. 12.
Li, X., et al., "A fast neutron deletion mutagenesis-based reverse genetics system for plants," The Plant Journal (2001), p. 235-242, vol. 27, No. 3.
Li, X., et al., "Reverse genetics by fast neutron mutagenesis in higher plants," Funct. Integr. Genomics (2002), p. 254-258, vol. 2.
McCallum, C.M., et al., "Targeting Induced Local Lesions in Genomes (TILLING) for Plant Functional Genomics," Plant Physiology (Jun. 2000), p. 439-442, vol. 123.
Zwaal, R.R., et al., "Target-selected gene inactivation in Caenorhabditis elegans by using a frozen transposon . . . ," Proc. Natl. Acad. Sci. USA (Aug. 2003), p. 7431-7435, vol. 90.

* cited by examiner

*Primary Examiner*—Ethan Whisenant
(74) *Attorney, Agent, or Firm*—Saliwanchik, Lloyd & Saliwanchik

(57) ABSTRACT

The subject invention relates to high-throughput methods of screening DNA for mutations. These methods offer various unexpected advantages over current methods. In a preferred embodiment, the subject invention includes pooling DNA samples from many plants that were subjected to mutagenesis. Methods of the subject invention include highly sensitive means for detecting individual mutants, preferably deletions, in large pools or collections of DNA samples.

31 Claims, 7 Drawing Sheets

Notes:
78°C is the annealing temperature for the PNA probe
Lane 5 contains product of deletion event.
Lane 6 contains PCR artifact
λ Hind II markers: 23130, 9416, 6557, 4361

Notes:
Lane 5 contains product of deletion event.
Residual wild-type product is visible in most other lanes
λ Hind II markers: 23130, 9416, 6557, 4361, 2322, 2027

HIGH-THROUGHPUT METHODS OF SCREENING DNA FOR DELETIONS AND OTHER MUTATIONS

CROSS-REFERENCE TO RELATED APPLICATION

The subject application claims priority to U.S. Provisional Application Ser. No. 60/472,863, filed May 22, 2003.

BACKGROUND

Since ancient times, mankind has been trying to improve the quality and yield of crops. In the 20$^{th}$ century, plant breeders developed mutation breeding as a tool for crop improvement. Breeders painstakingly examined progeny plants or seeds from mutagenized source material in hopes of finding lines with superior yield, grain quality, pest and stress resistance, and the like. Although these efforts had some degree of success (for example the dwarfing mutations that contributed to the Green Revolution of the 1960's), there was often little or no understanding of the underlying genetic changes that contributed to the improved traits. Success more or less reflected the random nature of mutagenesis and the ability of the investigators to recognize a plant with improved characteristics hidden among relatively large populations.

The recent convergence of multiple disciplines, such as molecular genetics, biochemistry and information science, has created a virtual explosion in the understanding of genes and their functions. The genomes of many organisms, including the plants Arabidopsis and rice, have been sequenced in their entirety; multiple varieties of transgenic crops with improved traits are now on the market or in development. However, given the cost of development and registration, as well as political opposition in some quarters, transgenic technology may not always provide the best solution for the goals of crop improvement. Although traditional crop breeding has benefited from the newer technologies, particularly in the areas of marker-assisted breeding and the identification of multiple loci in quantitative traits, classical mutation breeding has seen relatively few changes. By combining the expanding knowledge of gene function, the tools of molecular biology, and the techniques of classical mutagenesis, it is possible to create novel, non-transgenic approaches to crop improvement. Despite this potential, relatively few advances in that regard have been made thus far.

Although the entire genomes of some plants and other organisms have been sequenced, another great challenge that remains is identifying the function of genes that have not yet been characterized beyond the sequence level. One approach for identifying a gene's function is to "knock-out" the gene and observe the effect(s) this has on the plant. However, there are some limitations to the currently available techniques available for such approaches. For example, RNAi can be used in an attempt to silence a specific plant gene, but this "silencing" is often partial. Thus, it can be difficult to assess the effects of a gene "silenced" in this manner if partial expression remains.

A gene can also be "knocked out" by insertion of T-DNA or a transposable element into the gene or its regulatory region. Libraries of insertion mutants or lines can be generated (with each affecting a certain gene or genes), but a tremendous number of such insertion lines are typically required to span an entire genome. Creating insertions in small genes, or obtaining lines with insertions in two or more closely-linked genes, is also especially difficult or impossible. Furthermore, despite the fact that many of these techniques can be readily applied in the model plant Arabidopsis, and to a lesser extent in a limited number of other species such as maize, their utility in most crop species is often severely restricted or nonexistent.

U.S. Pat. No. 5,994,075 relates generally to methods for identifying a mutation in a gene of interest without a phenotypic guide. Some methods of inducing mutations in organisms and screening those organisms for mutations in genes of interest are known (Ballinger and Benzer S, 1989 Proc Natl Acad Sci U S A 86:9402-9406, Zwaal et al. 1993 Proc Natl Acad Sci USA 90:7431-7435), but those methods all have various limitations. For example, the presence of a T-DNA or transposon insertion (mentioned above) can be detected by polymerase chain reaction (PCR), which is a well-known technique that can be used for amplifying a targeted genetic region. However, transgenic and endogenous elements such as these are not widely available, and the techniques that use them have low detection sensitivity or require multiple screens to recover mutations.

Libraries of mutants can be generated in many ways, with the goal being mutants that span the genome. Various mutagens can be used to cause deletion mutants or other deleterious mutations. Point mutations can be difficult to screen and identify, although some techniques are reportedly available for such purposes. See, e.g., McCallum, C. M., L. Comai, E. A. Grene and S. Henikoff, "Targeting Induced Local Lesions in Genomes (TILLING) for plant functional genomics," Plant Physiology (June 2000), 123(2):429-442. See also WO 01/75167. PCR and sequencing of the amplicon is another technique, but this is obviously laborious and not amendable to high throughput.

Another approach for identifying mutations of interest is to use peptide nucleic acid (PNA) probes designed to target a certain sequence (typically of 18 residues or fewer) where a point mutation might occur. PNAs are nucleic acid analogues that can be designed to selectively bind conventional nucleic acids of complementary sequence to form hybrids that are more stable against dehybridisation by heat than are similar hybrids between conventional nucleic acids.

As explained in U.S. Pat. No. 5,891,625, a PNA probe can be designed as a diagnostic to bind strongly to a particular gene of a healthy individual but, in the case of a mismatch in the gene, lacks stable binding in individuals having a mutation in the gene. Thus, in a healthy individual, the PNA probe binds strongly to the gene and is effective to block PCR directed to that gene. On the other hand, the PNA probe will not maintain hybridization with an oncogenic mutation, allowing PCR amplification (with a resulting observable band) to proceed, thereby resulting in a PCR product that signals a dectectable oncogenic mutation. Alternatively, or in addition, such a PNA probe may be labeled, whereby the presence or absence of a label signals the absence or presence of a mutation.

DE 19733619 relates to the diagnosis of malignant tumors and to methods of assaying a small tissue sample from a known individual. The methods described therein generally involve the use of a PNA probe to detect oncogenic gene mutations. More specifically, the methods comprise: performing PCR using a complementary wild type analog PNA oligonucleotide which suppresses the amplification of surplus wild type alleles along with an oligodeoxynucleotide primer pair; and identifying the mutations or variations using PCR-RFLP (restriction fragment length polymorphism) and a known sequence for a restriction enzyme carrying oligonucleotide. When used for cancer detection, the PNA probe blocks PCR amplification of a sample from a cancer-free individual but permits PCR amplification of DNA from oncogenic cells having the known mutation(s). This method is said to be an improvement over PNA-mediated PCR clamping. Various limitations of PCR clamping are discussed in this reference, which adds a second step (PCR-RFLP) as an improvement The above-described PNA procedures, however, do not involve or suggest pooling DNA or using DNA samples from multiple sources. While these PNA procedures may be suitable for detecting point mutations in a given individual, different considerations are involved when screening large numbers of samples from multiple sources for unknown mutations (or deletions). This latter would be the case for screening a large collection of plants (1000+) that were subject to random mutagenesis. In this regard, screening an individual for cancer is quite different from screening large numbers of mutated plants, for example. Because the rate of mutation resulting from treatment with chemical mutagens and the like is relatively very low, high-throughput methods are needed in this context to screen large numbers of plants for unknown mutations.

PCR-based techniques have been developed to screen pooled samples for deletion mutants; however, this art has consistently taught that the extension time in the PCR procedure (i.e., the length of time that the polymerase is allowed to extend the DNA strand) must be shortened so as to preferentially amplify the shorter product from the deletion mutant but not the longer wild-type PCR product. In high-throughput versions of such screenings, samples from hundreds of mutated plants, for example, are pooled, and the pool is subsequently screened for the presence of a mutant. With this number of amplifications in mind, it is understandable that those in the art perceived it necessary to suppress the signal from the predominant wild-types by limiting the extension step of the PCR. See, e.g., U.S. Pat. No. 6,484,105; WO 98/50539; U.S. Pat. No. 6,358,690; WO 99/51774, U.S. Pat. No. 5,994,075; Xin Li et al. (The Plant Journal (2001), 27(3), 235-242), and Li & Zhang (Funct. Integr. Genomics (2002) 2:254-258). Many of these references involve attempts to identify the function of unknown genes having deletions therein.

Another limitation to these PCR techniques is that they are not sensitive enough to detect small deletions. That is, the PCR amplicon of a deletion mutant missing only 100 or so basepairs would not have a noticeably different band (as compared to the wild-type amplicon) on a typical gel (having resolving power to about 600 basepairs).

Edgley et al. note that only a small fraction of the sequenced nematode genes have been mutagenized. Nucleic Acids Research, 2002, Vol. 30, No. 12, e52. Edgely et al. attempt to "knock out" additional genes of nematodes (*Caenorhabditis elegans*) to create larger libraries to study the function of these genes, and to possibly find corresponding genes in humans. Edgley et al. used trimethylpsoralen (TMP)/ultraviolet light (UV) mutagenesis, which is reported to typically produce deletions in the range of 50-600 basepairs. TMP[UV mutagenesis is more suited for mutagenizing nematodes than plants, due to the inability of UV to penetrate plant seeds for example. This reference describes a technique using PCR and a third primer between the two external PCR primers to amplify DNA pooled from various nematodes mutated with TMP[UV. This technique was based on "nested PCR," which uses one set of primers in an initial round of PCR, followed by a second round of PCR using primers just inside of the first primers. The second step, which makes use of the nested primers, is performed so as to virtually eliminate the chances that a non-target amplicon produced in the first round would also be amplified in the second round. In the Edgley et al. approach, a third primer is used in the first round of PCR, wherein the third primer binds (in wild types) between the first set of primers. For wild-type templates, the third primer inhibits amplification between the two external primers, but allows amplification between the third primer and one of the external primers to occur. Thus, for wild type DNA, there is only amplification of a relatively short amplicon, which lacks a binding site for one of the nested primers for the second round.) However, if a deletion mutation removes the binding site of the third primer, PCR amplification between the two external primers occurs, resulting in a long amplicon. In the second round of PCR using the nested primers, only amplification of the long amplicon (containing the deletion mutation) occurs, thus signaling the presence of a deletion. The Edgely et al. approach is used for detecting small deletions in relatively short PCR amplicons in an organism amenable to mutagenesis methods that produce such deletions.

BRIEF SUMMARY OF THE INVENTION

The subject invention relates to high-throughput methods of screening for mutations, including deletions, in DNA. Preferably, plants are screened for desired mutations. These methods offer various unexpected advantages over previous methods, as explained in more detail below. The subject invention includes mutating tissues from plants (preferably seeds) or other organisms, extracting DNA samples therefrom to obtain a plurality of DNA sequences; amplifying the plurality of DNA sequences; and assaying the plurality of DNA sequences for the presence of mutated amplicons. Methods of the subject invention include highly sensitive means for detecting individual mutants in large pools of DNA from multiples sources.

In one embodiment, the subject invention provides "full-extension PCR" methods of using polymerase chain reaction (PCR) to detect deletion mutants (preferably in a pool of DNA samples). Thus, the subject invention includes a method of detecting mutagenized DNA, comprising: subjecting a plurality of DNA sequences to mutagenesis; amplifying the plurality of DNA sequences to allow full extension of non-mutagenized DNA, and less than full extension of mutagenized DNA, in the plurality of DNA sequences; and assaying the plurality of DNA sequences for the presence of mutated amplicons by detecting size differences between amplicons from the mutagenized DNA and the non-mutagenized DNA. In preferred methods, the extension step of the PCR reaction is allowed to progress to completion (thereby fully amplifying wild-type DNA), rather than being shortened to favor amplification of mutants and the production of truncated amplicons. One unexpected advantage this method provides over current (heretofore) teachings is that it includes a built-in positive control, which confirms that the PCR is proceeding correctly.

The subject invention also includes methods of detecting mutagenized DNA, comprising: subjecting a plurality of DNA sequences to mutagenesis; amplifying the plurality of DNA sequences to allow full extension of mutagenized DNA, and less than full extension of non-mutagenized DNA, in the plurality of DNA sequences; and assaying the plurality of DNA sequences for the presence of mutated amplicons by detecting size differences between amplicons from the mutagenized DNA and the non-mutagenized DNA.

In preferred embodiments, the subject invention provides methods of optimizing and improving the general strategies discussed above. In one such example of a preferred embodiment, the subject invention provides unique methods of blocking PCR amplification of wild-type DNA (preferably from plants, in a mixed pool), which results in the preferential amplification of mutant DNA. Thus, in situations where it is desirable to preferentially amplify mutants (preferably deletions) in mixed pools of plant DNA, the subject invention provides the unique approach of using peptide nucleic acid (PNA) probes to block PCR amplification of wild-type DNA. This approach is novel in this context and provides several unexpected advantages over techniques that are currently (heretofore) used to selectively amplify deletion mutants in large pools of mixed DNA.

In a further preferred embodiment, the subject invention provides methods of using PCR and a "poison primer" to yield a unique amplicon that signals the presence or absence of a mutation that removes the binding site of the poison primer. These methods provide surprising advantages (described below in more detail), and are surprisingly applied to plants in preferred embodiments. These methods are also preferably coupled with the novel use of preferred mutagens.

In yet another preferred embodiment, the subject invention provides a system referred to herein as gene mutation scanning (GMS). This approach can involve a first PCR step to amplify genomic DNA of interest. Generally with this approach, DNA (preferably genomic DNA) is digested by at least one restriction enzyme. One or more primers are designed and hybridized to each restriction fragment in such a manner so that PCR amplification (from a second PCR step if a first PCR step is used before restriction digestion) occurs only if there was a mutation that removed a restriction site.

In a preferred embodiment, fast neutron mutagenesis is utilized to create a mutant population to be screened.

One of skill in the art will recognize that these methods can be adapted to a wide variety of applications. Preferably, the methods of the subject application are used to screen deletion (and other) mutants of plants.

BRIEF DESCRIPTION OF THE SEQUENCES

Figure 1:
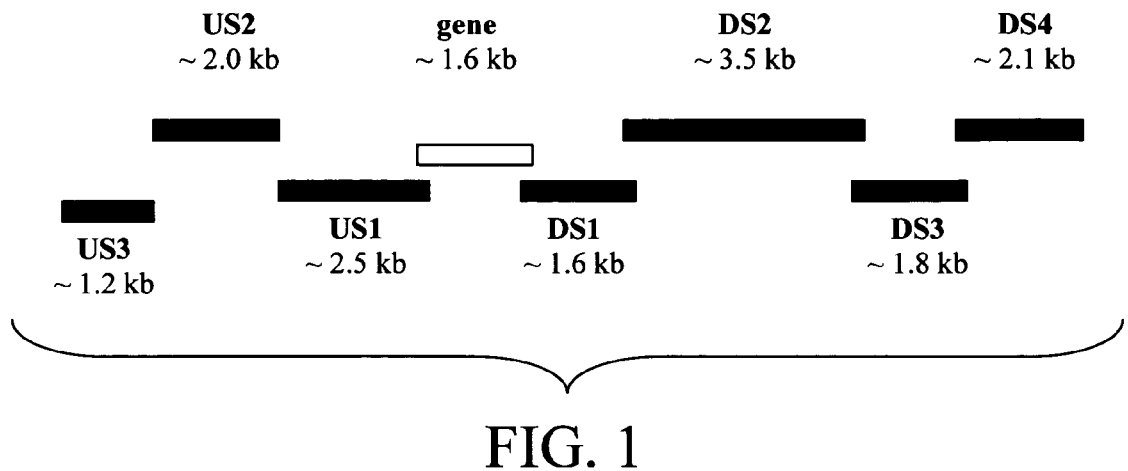
FIG. 1 is a diagram of steps taken using the GenomeWalker™ method to obtain DNA flanking the target gene for long PCR screening. [0023]

SEQ ID NO:1 is a primer used in Example 5.
SEQ ID NO:2 is a primer used in Example 5.
SEQ ID NO:3 is a PNA probe used in Example 5.
SEQ ID NO:4 is a PNA probe used in Example 5.
SEQ ID NO:5 is primer D199 (sense primer, aligns at approximately residue [2,101-] of GENBANK Accession No. AJ245480).
SEQ ID NO:6 is primer D200 (antisense primer, aligns at approximately residue [-19,162] of GENBANK Accession No. AJ245480).
SEQ ID NO:7 is PNA probe Q108.
SEQ ID NO:8 is primer D249 (sense primer for poison primer test, aligns at approximately residue [14,828-] of GENBANK Accession No. AJ245480).
SEQ ID NO:9 is primer D245 (sense primer, aligns at approximately residue [2,243-] of GENBANK Accession No. AJ245480).
SEQ ID NO:10 is primer D190 (Sense primer, aligns at approximately residue [-16,230] of GENBANK Accession No. AJ245480).
SEQ ID NO:11 is primer D195 (Sense primer, aligns at approximately residue [11,851-] of GENBANK Accession No. AJ245480).
SEQ ID NO:12 is primer D201 (Sense primer, aligns at approximately residue [12,650-] of GENBANK Accession No. AJ245480).
SEQ ID NO:13 is primer D209 (Sense primer, aligns at approximately residue [15,443-] of GENBANK Accession No. AJ245480).

DETAILED DESCRIPTION OF THE INVENTION

One method of increasing genetic diversity in crops to develop varieties with improved qualities and traits is through mutagenesis. As described herein, plants and/or seeds can be mutagenized and their progeny/descendants screened for, preferably, deletions in genes of interest. Methods of screening for plant mutants typically require breeders to examine thousands of plants or seeds for phenotypic variations, which usually appear in less than 25% of individual plants carrying some rare, beneficial mutation. Instead, preferred embodiments of the subject invention provide the same (or better) end results much more quickly using microtiter plates (and the like) to screen for desired mutants with traits of interest in almost any type of plant.

The subject invention relates to high-throughput methods of screening for mutations, including deletions, in DNA. Preferably, plants are screened for desired mutations in genes of interest. These methods offer various unexpected advantages over previous methods. The subject invention can include mutating plants or tissues therefrom (preferably seeds or pollen) to create M1 seeds and plants, pollinating the M1 plants to obtain M2 seeds, extracting DNA samples from M2 seeds or plants, and pooling the DNA samples from up to a thousand or so individuals. Methods of the subject invention provide highly sensitive means for detecting individual mutants in large pools.

The methods described in more detail below can be adapted to a wide variety of applications, including cancer detection. Preferably, the methods of the subject invention are used to screen deletion (and other) mutants of plants. Preferred plants for use with methods of the present invention include, but are not limited to, *Arabidopsis*, corn or maize, *Brassica* species (e.g. canola), wheat, cotton, soybeans, sorghum, fruits, vegetables (including tomatoes), legumes, castorbeans, grasses, rice, barley, and sunflowers. Mutagenesis is not required for some applications of the subject invention. For example, methods discussed below (preferably the PNA method and the. GMS method) can be used to study gene evolution in pedigrees, wild germplasm, and species variants and varieties.

If mutagenesis is desired, fast neutron mutagenesis (FN) is the preferred methodology for creating mutant populations to be screened according to the methods described herein. This mutagen is well known. See, e.g., Bruggemann et al. Plant J (1996) 10:755-760, Xin Li et al. (The Plant Journal (2001), 27(3), 235-242), and Li & Zhang (Funct. Integr. Genomics (2002) 2:254-258). Although FN techniques are known, the combination of FN with the methods described herein is novel and surprisingly advantageous. While FN is a preferred mutagen, many other type of mutagens can be used or adapted for use according to the teachings of the subject invention. Other preferred mutagens are those that cause detectable (as described herein) deletions in a gene or regulatory element of interest. Aside from FN, other radiation-type mutagens include X-rays, gamma-rays, UV, and the like. FN can typically be expected to produce deletions in the approximate size range of a few hundred base pairs to several thousand base pairs or more. Trymethylpsoralen (TMP)/UV generates smaller deletions than FN, as discussed above in the Background Section (Section 1). Chemical mutagens (most of which produce point mutations, but some of which also cause deletions at some frequency) include: diepoxybutane (DEB), diepoxyoctane (DEO), ethyl methanesulfonate (EMS), N-ethyl-N-nitrosourea (ENU), N-methyl-N nitrosourea (MNU), methylmethane sulfonate (MMS), and the like.

As previously described herein, gene knockouts have been associated with certain improvements in desirable attributes and traits of crops and other plants of interest. One skilled in the art will recognize that the present invention may be used to detect knockouts of certain genes and/or regulatory regions thereof that can improve traits and qualities in crops and other plants of interest. For example, certain proteins or metabolites are known to impart undesirable flavors, allergenic properties, or reduced nutritional quality to various parts of plants that are consumed by humans or farm animals. Thus, knocking out a particular gene in a pathway that gives rise to the undesirable protein or metabolite may act to improve the desirable qualities of the plant.

Alternatively, and according to the subject invention, one can screen for deletions in regulatory elements of genes of interest. Desirable deletions of this type can either, for example, knock out promotion or expression of an undesirable gene or a gene in an undesirable pathway, or they can knock out a regulatory element or gene responsible for the suppression of the activity of a gene (or genes) responsible for desirable qualities. Thus, desirable types of fatty acids, oils, proteins, and/or carbohydrates, for example, can be increased in this manner.

There are many specific examples of such targets. For example, allergenic proteins are known to exist in peanuts and other crops. Glucosinolates and sinapine impart an off-flavor to some products derived from Brassica species. Excess polyunsaturated oils can cause oil to become rancid. Another example is phytic acid, which can inhibit uptake of nutrients and also contributes to phosphate pollution.

In any of the approaches described below, as would be known in the art in light of the subject disclosure, running PCR products on a gel and observing the presence or absence of a band is not necessary. The presence of PCR-amplified product can simply be detected in a well be known techniques (such as by the use of dyes, stains, fluorescens and luminescens, or any other means for detecting the presence or absence of an amount of DNA).

Furthermore, as will be clear to one skilled in the art having the benefit of the subject disclosure, mutagenizing DNA is not required. Methods of the subject invention can be applied in other situations, such as detecting oncogenes and the like. Thus, DNA from a variety of sources (including humans) can be screened according to the subject invention. Likewise, DNA from a variety of sources can be mutagenized and screened according to the subject invention.

Examples of such sources are listed below in Section 5A. Mutagenizing tissues and tissue samples from such organisms (including the whole organism itself) is one way of "mutagenizing DNA" for use according to the subject invention. It should also be understood that nucleic acids other than DNA (RNA, for example) can be used in place of "DNA" as referred to throughout this disclosure.

As described below, the subject invention includes a method of detecting mutagenized DNA, comprising subjecting a plurality of DNA sequences to mutagenesis; amplifying the plurality of DNA sequences to allow full extension of non-mutagenized DNA, and less than full extension of mutagenized DNA, in the plurality of DNA sequences; and assaying the plurality of DNA sequences for the presence of mutated amplicons by detecting size differences between amplicons from the mutagenized DNA and the non-mutagenized DNA. The subject invention also includes methods of detecting mutagenized DNA, comprising: subjecting a plurality of DNA sequences to mutagenesis; amplifying the plurality of DNA sequences to allow full extension of mutagenized DNA, and less than full extension of non-mutagenized DNA, in the plurality of DNA sequences; and assaying the plurality of DNA sequences for the presence of mutated amplicons by detecting size differences between amplicons from the mutagenized DNA and the non-mutagenized DNA.

5A. Full-Extension PCR Approach

In one embodiment, the subject invention provides methods of using polymerase chain reaction (PCR) to detect deletion mutants in a collection of DNA samples (preferably pooled DNA samples) wherein the extension step of the PCR reaction is allowed to progress to completion (to fully amplify wild-type DNA), rather than being shortened to favor amplification of deletion mutants and the production of truncated amplicons. This is directly contrary to, and has unexpected advantages over, current (heretofore) teachings.

Polymerase Chain Reaction (PCR) is a repetitive, enzymatic, primed synthesis of a nucleic acid sequence. This procedure is well known and commonly used by those skilled in this art (see, e.g., Mullis, U.S. Pat. Nos. 4,683,195, 4,683,202, and 4,800,159; Saiki et al., 1985, and *PCR Protocols: A Guide to Methods and Applications* (Innis, M., Gelfand, D., Sninsky, J., and White, T., Eds.), Academic Press, San Diego (1990)). PCR is based on the enzymatic amplification of a DNA fragment of interest that is flanked by two oligonucleotide primers that hybridize to opposite strands of the target sequence. The primers are oriented such that extension from the 3' hydroxy terminus of each primer is directed towards the other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer serves as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium Thermus aquaticus, the amplification process can be completely automated.

According to the subject invention, preferred polymerases are able to (quickly) amplify long segments (16 kb-20 kb for example) of DNA by PCR. This offers advantages that the art taught were not possible, as the art taught that the PCR extension step must be shortened to prevent amplification of the wild-type (full-length) DNA. An example of a preferred polymerase for long-range PCR is discussed in the Examples section, below. One advantage of the subject invention is that it allows for amplifying longer regions of DNA, and thus increases the window that can be screened for a deletion, as compared to prior methods.

Without shortening the extension step, which allows amplification of wild-type DNA, this aspect of the subject invention also provides a built-in control. This allows one to easily check, without performing a separate reaction, whether the PCR is in fact proceeding correctly (should no mutants be detected in a given sample).

Thus, the subject invention includes the following:

A method of detecting a deletion mutant in a pool of DNA from a plurality of plants, wherein said method comprises the steps of:
 a) subjecting a plurality of plant seeds to mutagenesis to obtain M1 seeds;
 b) planting a plurality of said M1 seeds and growing M1 plants;
 c) pollinating a plurality of said M1 plants to produce M2 seeds;
 d) obtaining a DNA sample from each of a plurality of said M2 seeds (or from M2 plants obtained by the further step of growing M2 plants from a plurality of said M2 seeds);
 e) pooling said DNA samples to create pooled DNA;
 f) assaying said pooled DNA by PCR to obtain PCR samples, wherein said PCR comprises the steps of
  a. hybridizing primers, and
  b. performing PCR amplification to allow full amplification of wild-type DNA present in said pooled DNA;
 g) running said PCR samples on a resolving gel; and
 h) analyzing said gel for the presence of a band indicative of a deletion mutant present in said pooled DNA.

This method, and the other methods of the subject invention, can be followed by steps of tracing back the PCR results to the M2 (for example) family that was the source of the DNA sample where the deletion was identified. (U.S. Pat. No. 6,484,105, for example, discusses how databases can be used for this; e.g. insertion libraries in *Drosophphila* or *C. elegans* require such a structure to trace back from a DNA "hit" to recover the organism containing the mutation.)

Likewise for all the methods of the subject invention, this can be followed by planting the M2 seed (for example) and examining plants having the deletion for the trait of interest. Thus, the mutant DNA is traced back to the seed, for example, to recover a viable line that contains the deletion. In the case of a recessive phenotype, those lines would need to be screened for homozygous individuals where the trait could be assessed.

Steps g) and h) above are directed to a gel electrophoresis. However, steps g) and h) can be omitted and replaced with the step of simply detecting the presence or absence of PCR-amplified DNA. This can be done by a plate-based fluorescent assay, for example, as is known in the art.

Other variations of this preferred method can also be conducted according to the subject invention. For example, with reference to steps e) and f) above, the DNA samples do not actually have to be pooled. These steps can instead be performed on a "collection" of DNA samples, with each sample being in a microtiter plate well, for example. Thus, the DNA samples do not actually have to be mixed to form a single pool. Instead, a collection (a plurality of DNA samples) can be screened using known techniques, in light of the subject disclosure.

In addition, steps a)-d) can be substituted with the simple steps of obtaining a DNA sample from tissue from a plurality of plants. This tissue can be from pollen, seedlings, leaves, and the like, in addition to M2 seeds. For that matter, further generation of plants and/or seeds can be produced (e.g., M3, M4, M5, M6, etc.) and used as the source of the DNA sample. M1 seed can also be used according to the subject invention. Instead of using seed as the source of mutagenized DNA, mutated pollen can be produced and then used in step c), thereby removing or altering exemplified steps a)-c).

Still further, the methods of the subject invention are not limited to plant DNA. DNA from almost any organism (bacteria, fungi, nematodes, and animals including mice, rats, hamsters, and humans) can be used according to the subject invention. Almost any organism (cells therefrom) can be mutated and screened according to the subject invention, together with what was known in the art. The mutation step can also be eliminated for diagnostic applications, such as cancer detection in humans. Pooling of such samples might be eliminated in such applications.

Where mutagenesis is to be used, fast neutron (FN) mutagenesis is preferred. As used herein, a "plurality" can include 10, 100, 1000, or more. PCR conditions and time can be adjusted to allow for more or less amplification of the wild-type DNA. Some amplification of wild-type DNA is surprisingly desirable to provide a control; however, conditions can be adjusted so that only a faint band is obtained for wild-type to confirm that the PCR is properly functioning. It should also be understood that "wild type" as used herein typically refers to full-length DNA, as compared to deletion mutants. However, it should be understood that wild type DNA can actually be shorter than the target being screened for according to the subject invention. This is exemplified by FIG. 2 and in Example 4, which uses a transgenic plant containing a heterologous PAT insert as the "wild type"; DNA lacking this insert is the target of that screen. "Wild type" is used throughout this disclosure for ease of reference and to avoid confusion, but with the foregoing understood.

5B. PNA Approach

Although it was surprisingly found to be unnecessary (and advantageous) to limit or eliminate the amplification of wild-type DNA in mixed pools, there can be some advantages to preventing or inhibiting the amplification of wild-type (full-length) DNA. The subject invention provides unique methods of blocking PCR amplification of DNA from wild-type plants in a mixed pool so that deletion mutants are preferentially amplified. Thus, in situations where it is desirable to preferentially amplify deletion mutants in mixed pools of plant DNA, the subject invention provides the unique approach of using peptide nucleic acid (PNA) probes to block PCR amplification of wild-type DNA in mixed pools of multiple plant DNA. This approach is novel in this context and provides several unexpected advantages over techniques that are currently (heretofore) used to selectively amplify deletion mutants in large pools of mixed DNA.

PNA probes, themselves, are well-known in the art. See, e.g., U.S. Pat. No. 5,891,625. In practice, the maximum size of PNA probes is approximately 18 nucleic acid residues. PNA probes according to the subject invention can be designed to target almost any gene of interest so that deletions in the gene of interest can be detected. Alternatively, LNA probes, for example, can be adapted for use in the same manner as the exemplified (and preferred) PNA probes. Thus, the subject invention includes the use of LNA probes in place of PNA probes according to the other teachings of this invention.

This approach is more sensitive to smaller deletions than is the PNA-free PCR approach discussed above. This is discussed at the end of Example 5.

Thus, the subject invention includes:

A method of detecting a deletion mutant in a pool of DNA from a plurality of plants, wherein said method comprises the steps of:
 a) subjecting a plurality of plant seeds to mutagenesis to obtain M1 seeds;
 b) planting a plurality of said M1 seeds and growing M1 plants;
 c) pollinating a plurality of said M1 plants to produce M2 seeds;
 d) obtaining a DNA sample from each of a plurality of said M2 seeds (or from M2 plants obtained by the further step of growing M2 plants from a plurality of said M2 seeds);
 e) pooling said DNA samples to create pooled DNA;
 f) providing a PNA probe to said pooled DNA wherein said PNA probe is designed to hybridize to a gene or regulatory element of interest;
 g) assaying said pooled DNA by PCR wherein PCR amplification proceeds in the absence of bound PNA, and PCR amplification does not proceed in the absence of bound PNA (thereby indicating the presence of a deletion that removes the PNA binding site);
 h) running said PCR samples on a resolving gel; and
 i) analyzing said gel for the presence of a band indicative of a deletion mutant present in said pooled DNA.

Steps h) and i) can be omitted and replaced with a step of simply detecting the presence or absence of PCR-amplified DNA. A plate-based fluorescent assay, for example, can be used.

Fast neutron (FN) mutagenesis is preferred. Hybridization and other conditions can be adjusted to allow for partial blockage of the wild-type PCR by the PNA probe. Thus, a positive control can be obtained in this manner. Complete blockage of the wild-type PCR by the PNA probe is not necessary.

This approach can also be used to detect mutants other than deletion mutants. Point mutants, for example, can "knock out" the PNA binding site (or a primer binding site) which would also be detectable by the subject PNA method. (The full-extension PCR approach is more suited to detect deletions rather than point mutations.) Thus, the subject PNA method lends itself to diagnostic applications, such as cancer detection, in which case the mutagenizing step a) would not be performed. Methods omitting step a) are within the scope of the subject invention, as well.

As with the full-extension PCR approach, the subject PNA approach is not limited to plant DNA but can be used with other organisms. Steps a)-d) can be replaced with the step of obtaining DNA from an organism that was subject to mutation. M1, M3, M4, M5 and seeds from even subsequent generations (where either mutated seed, pollen, or plant was a parent) can be used in any of the exemplified steps. Again, the DNA samples do not have to be mixed in a single pool; a collection of DNA samples in separate wells or microtiter plates, for example, can be used. However, in some applications, a sample from a single individual could also be screened according to the subject invention. Instead of using M1 seed, mutated pollen can be obtained and used in step c), thereby removing or altering exemplified steps a)-c).

5C. "Poison Primer" Approach

In a further preferred embodiment, the subject invention provides methods of using PCR and a "poison primer" followed by a nested PCR reaction. These methods are surprisingly applied to plants, preferably, and are coupled with the novel use of preferred mutagens.

As described in Example 6, this approach modifies the traditional two-stage nested PCR procedures by adding at least one additional primer that binds between the two outer primers of the primary PCR. This "poison primer" is designed to hybridize to the target gene and, together with one of the outer primers, leads to the formation of a PCR "poison product" that is substantially smaller than the size of a product formed between the two outer primers in the next step. Due to the kinetic advantage (as discussed in Example 5), the shorter poison product will predominate in the primary PCR. When this primary product is used as a template in the secondary reaction, little or no full-length product is formed because a binding site for one of the two nested primers does not exist on the poison product. If however, a deletion removes the binding site for the poison primer (but not any binding sites for the nested or outer primers), the poison product can no longer form in the primary PCR. In the secondary PCR, both nested primers will bind to the primary template and lead to formation of a product that signals the presence of the deletion.

Use of this approach in the context of pooled plant DNA, especially when combined with FN mutagenesis, is novel. TMP/UV, for example, is not suited for mutagenizing seeds and plants due to its lack of penetrability. Furthermore, TMP/UV mutagenesis generates smaller deletions, and smaller PCR windows (closer primers) must be used. As is apparent based on the subject disclosure, it is presently taught that screening large (long) windows with PCR is preferred (though not essential), because larger windows are more likely to "catch" a given deletion (in fewer steps). Thus, the use of mutagens such as FN that generate large deletions, coupled with this approach, is a novel and unexpected combination.

In a highly preferred embodiment of this approach, which offers further advantages over prior nested PCR approaches, two PCR steps are not required. The results of the first PCR amplification with the "poison primer" can be assayed for the presence of a relatively long amplicon, thus indicating the presence of a mutation that removed the binding site of the poison primer (which would block amplification/production of the long amplicon). This approach is much more efficient, cheaper, and quicker than a nested PCR approach and other related approaches as previously taught in the art.

Thus, the subject invention includes:

A method of detecting a deletion mutant in a pool of DNA from a plurality of plants, wherein said method comprises the steps of:
   a) subjecting a plurality of plant seeds to mutagenesis (fast neutron mutagenesis is preferred) to obtain M1 seeds;
   b) planting a plurality of said M1 seeds and growing M1 plants;
   c) pollinating a plurality of said M1 plants to produce M2 seeds;
   d) obtaining a DNA sample from each of a plurality of said M2 seeds (or from M2 plants obtained by the further step of growing M2 plants from a plurality of said M2 seeds);
   e) pooling said DNA samples to create pooled DNA;
   f) providing a first pair of PCR primers designed to hybridize to said DNA;
   g) providing a third primer designed to hybridize between said first pair of PCR primers;
   h) performing PCR amplification with said pooled DNA, said first primer pair, and said third primer (whereby amplification occurs from said first primer pair in the absence of binding of the third primer, the absence of binding of the third primer being due to a deletion that removes the binding site of said third primer);
   i) providing a second pair of PCR primers designed to be nested within said first PCR primers;
   j) performing PCR amplification with said second pair of PCR primers and said pooled DNA; and
   k) assaying said pooled DNA for the presence of an amplicon resulting from amplification from said second PCR primer pair (wherein the lack of said amplicon indicates the presence of a deletion that removed the binding site of said third primer).

This approach can also be used to detect mutants other than deletion mutants. Point mutants, for example, can "knock out" the "poison primer" binding site which would also be detectable by the subject method. Steps a)-d) can be replaced with the step of obtaining DNA from M1, M3, M4, and M5 plants and seeds. Seeds and plants from even subsequent generations can be substituted for use in the exemplified steps. Again, the DNA samples do not have to be mixed in a single pool; a collection of DNA samples in separate wells or microtiter plates, for example, can be used. Instead of using M1 seed, mutated pollen can be used in step c), thereby removing or altering exemplified steps a)-c).

This approach is also not limited to plants, although such applications are preferred. One skilled in the art will recognize that DNA from other organisms, including humans, can be used in the methods of the present invention. Furthermore, in some applications, the mutagenesis step is not essential, as would be the case if these methods are used to detect an oncogene, for example.

5D. Gene Mutation Scanning

In yet another preferred embodiment, the subject invention provides a system referred to herein as gene mutation scanning (GMS). In this approach, a first PCR step can be performed. Generally with this approach, DNA (including genomic DNA amplified by said first PCR step, if that is desired) is subjected to digestion by at least one restriction enzyme. In preferred embodiments of this approach, one or more primers are designed and hybridized to each restriction fragment, followed by a PCR step (a second PCR step if a first PCR step is performed), so that amplification by the (second) PCR step occurs only in the presence of a deletion that removed a restriction site. This approach is explained in much more detail below in Example 7.

Thus, the subject invention includes:

A method of detecting a mutant (including deletion mutants and point mutants) in a pool of DNA from a plurality of plants, wherein said method comprises the steps of:
   a) subjecting a plurality of plant seeds to mutagenesis to obtain M1 seeds;
   b) planting a plurality of said M1 seeds and growing M1 plants;
   c) pollinating a plurality of said M1 plants to produce M2 seeds;
   d) obtaining a DNA sample from each of a plurality of said M2 seeds (or from M2 plants obtained by the further step of growing M2 plants from a plurality of said M2 seeds);
   e) pooling said DNA samples to create pooled DNA;
   f) providing a first pair of PCR primers designed to hybridize to said DNA;
   g) performing PCR amplification with said pooled DNA and said first primer pair to obtain a primary amplicon;
   h) digesting the amplified PCR product with at least one restriction enzyme to obtain a plurality of restriction fragments;
   i) providing a plurality of RF primers, each said RF primer being designed to hybridize to a restriction fragment, wherein a deletion of a restriction site in said primary amplicon allows PCR amplification by two or more of said RF primers of a secondary amplicon, and wherein no amplification of a secondary amplicon by two or more of said RF primers occurs in the absence of a deletion removing a restriction site in said primary amplicon;
   j) performing PCR amplification with said restriction fragments and said RF primers; and
   k) assaying said pooled DNA (by gel electrophoresis or microtiter-based fluorescent assay, for example) for the presence or absence of a secondary amplicon resulting from amplification from said RF primers (wherein the presence of said secondary amplicon indicates the presence of a mutation (including a deletion) that removed a restriction site from said primary amplicon).

The subject approach does not require the first PCR amplification of steps f) and g). That is, genomic DNA can be digested directly with the restriction enzymes, and the resulting fragments can be used for the PCR amplification of steps i) and j). Furthermore, this approach can also be used to detect mutants other than deletion mutants. Point mutants, for example, can "knock out" the restriction enzyme cut site (or a primer binding site) which would also be detectable by the subject method. The subject approach is also not limited to plant DNA but can be used with DNA from other organisms. Steps a)-d) can be replaced with the step of obtaining DNA from an organism that was subject to mutation. Mutagenesis, however, is not a required step. This would be the case if these methods are adopted for diagnosing cancer, for example. Because applications in the plant breeding context are preferred, M1, M3, M4, and M5 plants and seeds, and seeds and plants from even subsequent generations (where either mutated seed, pollen, or plant was a parent) can be used in any of the exemplified steps. Instead of using M1 seed, mutated pollen can be produced and used in step c), thereby removing or altering exemplified steps a)-c). Again, the DNA samples do not have to be mixed in a single pool; a collection of DNA samples in separate wells or microtiter plates, for example, can be used. DNA from a single individual can also be tested alone, if desired.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Creation of Fast Neutron-Mutagenesis-Derived Canola Seed Bank and DNA Libraries

This example shows how a collection of seed and corresponding DNA samples were created. Canola seed (*Brassica napus*) was treated with 50-60 Gy of fast neutrons (KFKI Atomic Energy Research Institute, Budapest, Hungary). The resulting $M_1$ seeds were planted and each $M_1$ plant was harvested individually to give an $M_2$ family. Each $M_2$ family was placed in a numbered envelope for long-term storage and retrieval. Seeds of five $M_2$ families, sampled at the rate of approximately 4-5 $M_2$ seeds per family, were placed in each well of a 9-2 ml deep-well plate (Fisher). A 4-mm tungsten ball was added to each well and the (dry) seeds were ground by agitating the plate on a shaker (Kleco). DNA was extracted and purified using a commercial kit (Qiagen DNeasy Plant 96) following the manufacturer's protocol with modifications. Briefly, the ground seed material in each well was incubated for 1 h at 60° C. in 500 μl of buffer AP1 with RNase and reagent DX as specified by the manufacturer plus 10 mM of the antioxidant sodium metabisulfite. 150 μl of AP2 solution (Qiagen) was added, the mixture was held at −20° C. for 10 min and then centrifuged at 5600×g for 5 min. Approximately 450 μl of the supernatant from each well was transferred to the corresponding well of a new plate followed by 1.5 volumes of AP3/ethanol buffer (Qiagen). The mixtures were transferred to DNeasy 96 spin columns followed by a wash step as specified by the manufacturer but with the addition of a final wash using 800 μl of absolute ethanol per column and a 20 min centrifugation at 5600×g to dry the columns. DNA was eluted with 100 μl of buffer AE (Qiagen) to a primary plate. A second 100 μl elution was saved to a back-up plate.

EXAMPLE 2

Pooling DNA and Screening with Primers for Deletions

This example shows how DNA from the primary plates described in Example 1 were pooled and screened for deletions in a target gene. DNA from 3 wells of a primary plate were pooled into a single well of a secondary plate. At a sampling rate of 5 seeds per $M_2$ family and 5 $M_2$ families per well in the primary plate, a single well in a secondary plate represents 60 $M_2$ families and a heterozygous gene deletion event in a single seed would be represented at approximately 1 in 600 non-deleted gene copies. PCR amplifications were performed in 200 μl wells in a 25 μl reaction volume, using 2.0 μl of the pooled DNA (~50 ng) as a template plus other components as recommended by the manufacturer (TaKaRa): 1×LA PCR buffer, 3.0 mM $MgCl_2$, 400 μM each dNTP, 0.2 μM of each primer, and 1.2 U LA Taq. The thermocycler (MJ RESEARCH) was programmed for 94° C., 2 min followed by 30 cycles of 94° C., 20 sec; 68° C., 15 min. The primers as used supported amplification of an approximately 16 kb product. PCR products were visualized by running approximately one-half the reaction volume on a 0.5% agarose gel (SEA CHEM GOLD). In an initial screen of 88 samples representing DNA from 5,280 $M_2$ families, seven reactions yielded secondary products of approximately 11 kb. Because of the expected low frequency of deletions and the indication that these products were all the same size, it is likely these secondary products represent the same natural polymorphic allele. PCR analysis of respective primary samples for these products demonstrated that the PCR product identified in each secondary pooled sample originated in a single primary DNA sample derived from five $M_2$ families.

EXAMPLE 3

Preparation and Pooling of DNA for Detection of Mutant Lines Using Full-Extension PCR Gene targets are prepared by identification of an amplicon that contains the gene plus upstream and downstream flanking regions. Amplicon identification is achieved using a Universal GenomeWalker Kit (Clontech, Palo Alto, Calif.). The first step in this procedure is to obtain clean, high average molecular weight genomic DNA from canola tissue. Canola seeds are sown on 0.8% agar medium supplemented with ½ strength MS media and grown in a growth chamber with 12 hour light period at 25° C. and a 8 hour dark period at 15° C. After 7 days the seedlings are washed, blotted dry, ground to a fine powder in liquid $N_2$ with a mortar and pestle, and immersed (1 g/10 ml) in a CTAB buffer solution containing (100 mM Tris-HCL, pH 7.5, 25 mM EDTA, 2 M NaCl, 1.5% PVP 40[polyvinylpyrrolidone, Sigma, St. Louis, Mo.], and 2.5% CTAB [Hexadecyltrimethylammonium bromide, Sigma]. The solution is incubated for 2 hours at 65° C. After cooling to room temperature, 4.5 ml chloroform/octanol (24:1) is added and gently mixed for 5 min until both layers are mixed and dispersed, then centrifuged for 10 min at 2000 rpm. The top (aqueous) phase is transferred to a 15 ml polypropylene tube containing 6 ml ixopropanol and allowed to stand for 1 hour. The samples are gently mixed and then centrifuged at 10,000 rpm for 20 min to pellet the DNA. The supernatant is poured off and the pellet is re-suspended in 1 ml TE buffer. RNA is digested by adding 2 μl of a 10 μg/μl RNAse A solution and incubated at 37° C. for 1 hour. Polysaccharides and other debris are pelleted by centrifuging at 14,500 rpm for 10 min. The supernatant is separated to two 0.5 ml samples and to each is added 150 μl 10 M Ammonium Acetate and 500 μl isopropanol. The DNA is spooled with a glass rod, rinsed twice with 70% ethanol, blotted dry and resuspended in TE buffer. The concentration is determined using a Pico Green® dsDNA Quantitation Kit (Molecular Probes, Eugene, Oreg.) and the solution is diluted with more TE buffer to give a final concentration of 200 ng DNA/1 μl. The DNA is also tested for size and purity by running on a 0.5% agarose/ethidium bromide gel. This DNA is used to make the restriction digest libraries that are used for genome walking and as a template for PCR reactions.

Restriction digest libraries of Dra 1, EcoR V, Pvu 11 and Stu 1 are prepared by incubation at 37° C. for 2 hours of 2.5

μg canola genomic DNA, the restriction enzyme (80 units) and the respective restriction enzyme buffer in deionized water in a total of 100 μl. A control library using human genomic DNA and one of the restriction enzymes is also produced. After incubation 5 μl of the solutions are run on a 0.5% agarose/ethidium bromide gel to determine if the cuts are complete. The remaining 95 μl is mixed with phenol, vortexed at slow speed and spun briefly in a microcentrifuge. The upper (aqueous) layer is transferred to a clean 1.5 ml tube and mixed with 190 μl ice cold 95% ethanol, 9.5 μ3 M sodium oxaloacetate (pH5.2) and 20 μg glycogen. After centrifugation at 13,100 rpm for 15 min, the supernatants are decanted, and the pellets are washed with 100 μl ice cold 80% ethanol. The pellets are air-dried and dissolved in 20 μl 10 mM TE with 0.1 mM EDTA pH 7.5. Use 5 μl to run on 0.5% agarose/ethidium bromide gel to determine approximate quantity of DNA after purification. The final step in library preparation is ligation of the purified DNA. A ligation reaction of 4 μl digested, purified DNA, 1.9 μl GenomeWalker Adaptor (25 μM), 1.6 μl 10× Ligation Buffer and 0.5 μl T4 DNA Ligase (6 units/μl) is incubated at 16° C. overnight. The reactions are stopped by incubating at 70° C. for 5 min and then diluted by adding 72 μl 10 mM TE with 1 mM EDTA, pH 7.5. Each library solution is aliquoted and stored at minus 20° C.

Genome walking is conducted by utilizing primary and secondary PCR reactions.

Primers are designed, according to the GenomeWalker Kit specifications, for primary and secondary (or nested) PCR from the 5' (for walking upstream) and 3' (for walking downstream) ends of the gene to be walked. TaKaRa LA Taq™ (LA Taq, Takara Shuzo Co., Japan) is the DNA polymerase used for the PCR reactions. A primary PCR reaction consists of 0.5 μl restriction digest library (reactions for all 4 libraries are run concurrently), 0.5 μl of primary adaptor primer, 0.5 μl of primary gene primer, 2.5 μl 10×LA PCR buffer (with 25 mM Mg), 4 μl dNTP mix (2.5 mM each), 0.7 μl MgCl$_2$, 0.25 μl LA Taq (5 U/μl) and H$_2$O to make 25 μl total. Positive controls (with the human DNA restriction library constructed along with the other libraries and a human DNA restriction library supplied in the GenomeWalker Kit) are run with the supplied adaptor and gene primers. In addition, a negative control with the gene primer omitted is run to test if any products are produced with the adaptor primer alone. The primary reaction is performed using a PTC-220 DNA Engine Dyad™ Peltier Thermal Cycler (Dyad, M J Research, Boston) with the following cycling parameters:

1. 94° C., 25 sec
2. 72° C., 3 min
3. cycle 6 more times to step 1
4. 94° C., 25 sec
5. 65° C., 3 min
6. cycle 31 more times to step 4.
7. 65° C. 7 min
8. hold at 4° C.

Eight μl of the primary PCR reaction products are separated on a 1.0% agarose/ethidium bromide gel. When products and/or a smear are observed, proceed to the secondary reaction.

The secondary PCR reaction consists of 0.5 μl of a ⅟₅₀ dilution of the primary PCR reaction, 0.5 μl of secondary adaptor primer, 0.5 μl of secondary gene primer, 2.5 μl 10×LA PCR buffer (with 25 mM Mg), 4 μl dNTP mix (2.5 mM each), 0.7 μl MgCl$_2$, 0.25 μl LA Taq (5 U/μl) and H$_2$O to make 25 μl total. The secondary reaction is preformed on the Dyad with the following cycling parameters:

1. 94° C., 25 sec
2. 72° C., 3 min
3. cycle 4 more times to step 1
4. 94° C., 25 sec
5. 65° C., 3 min
6. cycle 19 more times to step 4.
7. 65° C. 7 min
8. hold at 4° C.

Five μl of the secondary PCR reaction products are separated on a 1.0% agarose/ethidium bromide gel. Secondary PCR products are either sequenced directly from the PCR reaction mixture after purification using a Performa® DTR Gel Filtration Cartridge (Gaithersbury, Md.) or sequenced after separation on and purification from (using a QIAquick Gel Extraction Kit, Qiagen Inc., Valencia, Calif.) a 0.5% agarose/ethidum bromide gel. Sequencing is performed using the Big Dye™ terminator cycle sequencing ready reaction (Applied Biosystems, Foster City, Calif.) according to the manufacturer's suggested protocol. The 5' sequence of the secondary PCR product is used to design primers for PCR of the PCR fragment plus the gene to show that they are contiguous, and to design primary and secondary primers for the next genome walking PCR reactions. The genome walking reactions and consequent PCR reactions are continued both upstream and downstream from the gene until the desired size of amplicon is identified. FIG. 1 shows an approximate 16 kb sample amplicon obtained for a sample gene from canola variety Nex 710.

A sense primer and an antisense primer designed from "US3" and "DS4" (upstream and downstream fragments, respectively, from the gene of interest; see FIG. 1) are used to obtain an approximate 16 kb PCR product. The PCR reaction mixture consists of 0.5 μl Canola Nex 710 genomic DNA (10 to 200 ng/μl) as template, 0.5 μl each of primers, 2.5 μl 10×LA PCR buffer (with 25 mM Mg), 4 μl dNTP mix (2.5 mM each), 0.7 μl MgCl$_2$, 0.25 μl LA Taq (5 U/μl) and H$_2$O to make 25 μl total. The PCR reaction is run on the Dyad Thermal Cycler with the following cylicing parameters:

1. 94° C. 2 min
2. 94° C. 20 sec
3. 68° C. 15 min
4. cycle 29 more times to step 2
5. hold at 4° C.

EXAMPLE 4

Sensitivity of detection of a Deleted Gene in Canola

To illustrate how the procedures of the subject invention work in practice, a transgenic plant DNA (with a marker gene insert) was used to simulate wild-type plant DNA, and wild-type plant DNA without the marker gene insert (to simulate a deletion event) was used to illustrate how a deletion would be identified.

Figure 2:
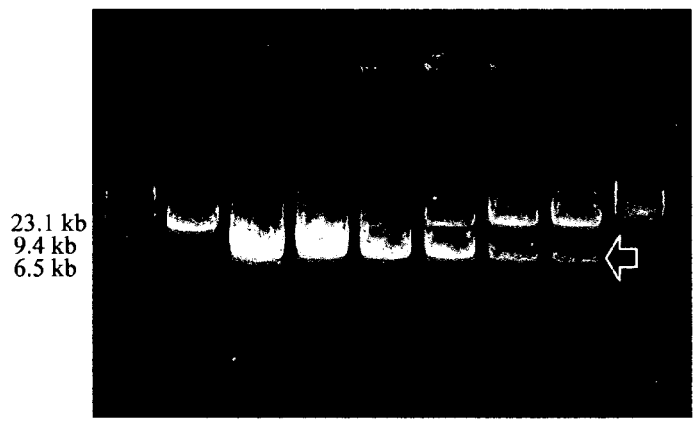
FIG. 2 shows PCR products of mixtures of wild type (non-transgenic canola with gene "deleted") and transgenic canola containing a 7 kb *Aspergillus* Δ9 desaturase/PAT insert using primers that produce a 16 kb amplicon containing the transgenic gene inserts. The amplicon with the "deleted" gene (lacking the PAT insert) is detected at a dilution of $1/1000^{th}$.

Sensitivity of detection of a deleted gene in canola was measured by the following procedure. Genomic DNA from a transgenic canola line that contains a gene for *Aspergillus* Δ9 desaturase (U.S. Pat. No. 6,495,738) and a gene for phosphenothricin transferase (PAT, selectable marker gene) was used to make restriction digest libraries for genome walking. Genome walking was performed both upstream and downstream of the 7 kb *Aspergillus* Δ9 desaturase/PAT insert. Primers were designed from the two outmost fragments that produce a 16 kb PCR product using the PCR reaction and cycling parameters described above. PCR reactions were performed using various dilutions of the wild type DNA (from non-transgenic canola, in this case representing DNA containing the "deleted" gene) with DNA from the *Aspergillus* Δ9 desaturase/PAT transgenic canola as templates. Dilutions of $1/10^{th}$ to $1/1000^{th}$ are tested. FIG. 2 shows the PCR products from this experiment. The PCR product from the "deleted" gene amplicon is clearly observed at a dilution of $1/1000^{th}$.

FIG. 2 shows PCR products of mixtures of wild type (non-transgenic canola with gene "deleted") and transgenic canola containing a 7 kb *Aspergillus* Δ9 desaturase/PAT insert using primers that produce a 16 kb amplicon containing the transgenic gene inserts. The amplicon with the "deleted" gene is detected at a dilution of $1/1000^{th}$.

EXAMPLE 5

Use of PNA Probes in the Detection of Deletion Mutants in Mixed DNA Pools

Figure 3:
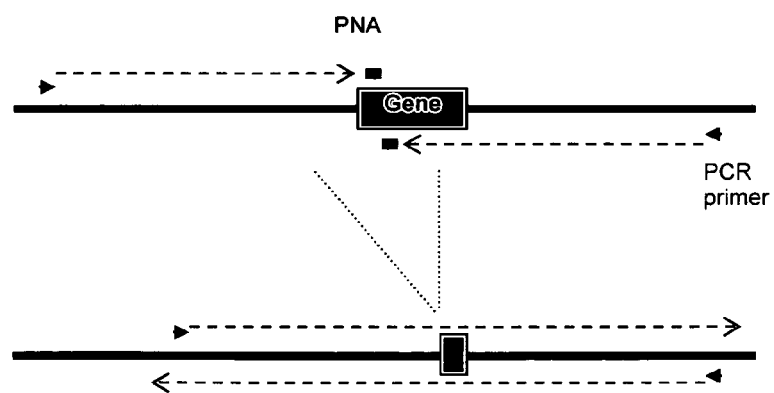
FIG. 3 is a basic illustration of the PNA approach.

This example shows how peptide nucleic acid (PNA) oligomers can be used to enhance the long-range PCR-based detection of DNA from a deletion mutant that is present as a minor fraction in a pool of DNA derived primarily from wild-type plant material. FIG. 3 shows a basic illustration of this technology, which is surprisingly and advantageously applied presently to the context of pooled plant DNA.

The Arabidopsis sng1-8 deletion event removes ~6 kb of DNA from the SNG1 locus (Lehfeldt et al. 2000, Plant Cell 12:1295-1306). Using published sequence information from the Arabidopsis genome, PCR primers upstream (GAATTATCTACTATGTGAGCTATTTGTTCCTGAG) (SEQ ID NO:1) and downstream (CCTTCATCTAATCAGAACATGTAAGTAGAATGTG) (SEQ ID NO:2) of the sng1-8 deletion were designed to produce a 19.1 kb amplicon that included the SNG1 gene and flanking regions. To inhibit PCR amplification of the wild-type SNG1 DNA, two PNA oligomers (CAAACTGAACCAAACCCG and TGGTTTCGGTATGATCCA) (SEQ ID NO:3 and SEQ ID NO:4, respectively) that were complementary to a region of the SNG1 gene known to be removed by the sng1-8 deletion, were synthesized (Applied Biosystems) for addition to PCR. PCR conditions were as recommended by the manufacturer of LA Taq (Takara) except that a 25 μl reaction volume, 3.2 mM Mg, 100 ng of template DNA, and 3.0 μM of each PNA oligomer were used. In addition, thermocycler parameters were modified from the 2-step protocol recommended by the manufacturer to include a 75° C. annealing step for the PNA oligomers: a single 94° C. 1 min denaturation step was followed by 30 cycles of 94° C. 20 sec, 75° C. 30 sec, 66° C. 12 min.

Figure 4:
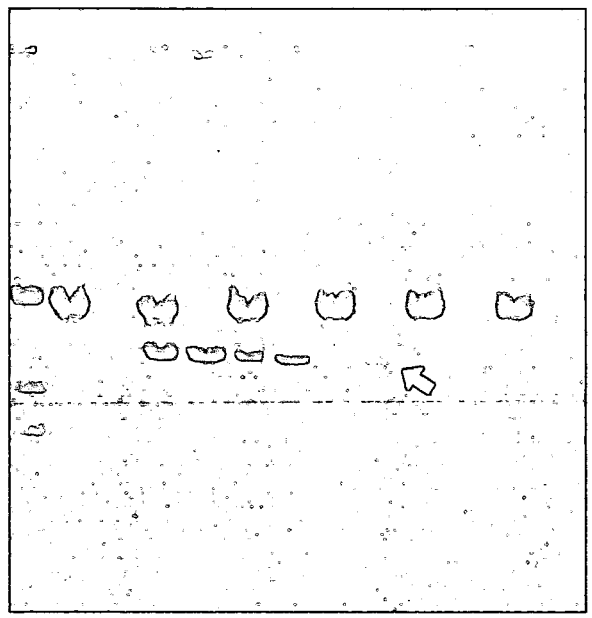
FIGS. 4 and 5 show detection of the Arabidopsis sng1-8 deletion. See Lehfeldt et al. 2000 Plant Cell 12:1295-1306.
Figure 5:
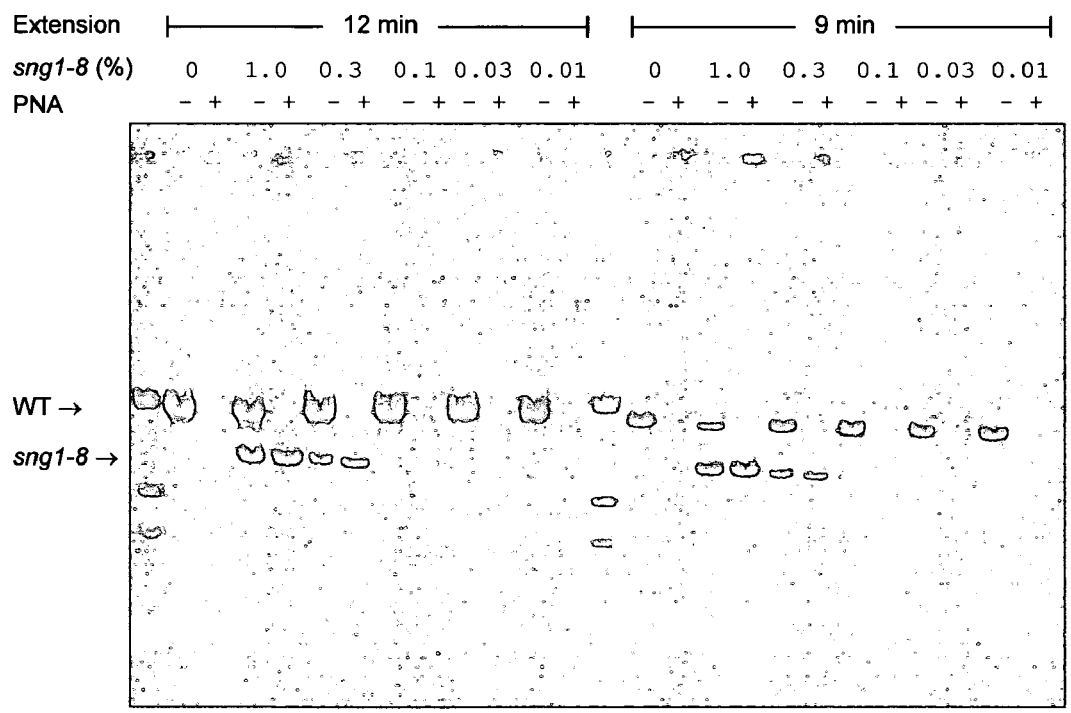

Under the conditions described above, the addition of the PNA oligomers to the reaction mix specifically inhibited synthesis of the 19.1 kb wild-type product but did not inhibit production of the 13 kb sng1-8 mutation-derived product. The mutant product could be detected from a PCR reaction where only 0.1 ng of sng1-8 DNA (0.1% of the total) was provided as a template. It should be noted that the 13 kb mutant product was still detectable, albeit at a lower level, from a nearly identical PCR that did not contain PNA oligomers. See FIGS. 4 and 5. The relative abundance of the 13 kb mutant product in this case is due to its kinetic advantage over the larger 19.1 kb wild-type product in PCR. Had the sng1-8 deletion been smaller (1 kb for example), the mutant product would have little kinetic advantage over the wild-type product and so would not likely have been detected without the addition of PNA oligomers to suppress formation of the wild-type product. (That is, with a large deletion, PCR amplification of a full-length wild-type segment takes longer for the polymerase to produce than a much shorter deletion mutant of that segment. Thus, with both templates—wild-type and deletion—in the same PCR, the shorter amplicon will be relatively much more abundant than the long wild-type after the PCR is allowed to proceed for some time. However, this would not be the case where the wild type and the deletion are close to the same size, as it would take the polymerase approximately the same time to traverse both of these segments.) This illustrates an advantage of the subject PNA approach.

Figure 6:
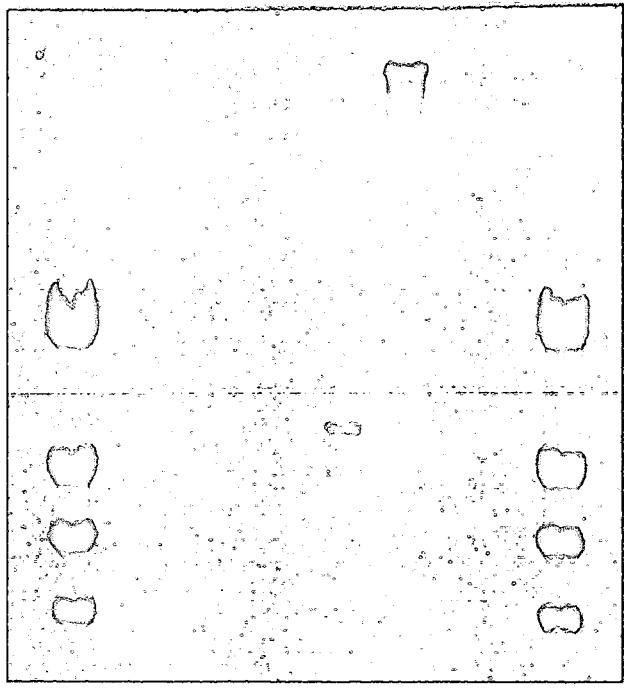
FIG. 6 shows an agarose gel exemplifying a PNA method of the subject invention used to identify a deletion in canola.

The PNA method was also used to detect a deletion in canola. These methods were exemplified using wild-type canola lines and a canola line having an approximately 2,325 bp deletion beginning with residue 13,544 of the 87,844 bp region in the canola genome corresponding to the sequence available from GENBANK as Accession No. AJ245480. Primers and PNA probes were designed to target this region. Eight samples, each containing approximately 15 ng of genomic DNA (pooled from samples representing 15 $M_2$ families sampled at the rate of approximately 5 seeds per family) were subjected to PCR using primers D199 (SEQ ID NO:5) and D200 (SEQ ID NO:6) plus 1 μM of PNA probe Q108 (SEQ ID NO:7) (Applied Biosystems). (The approximate location of these primers [and other primers described below] with respect to the sequence of GENBANK Accession No. AJ245480 are provided above in the Brief Description of the Sequences section.) PCR conditions were those recommended by the manufacturer for LA Taq (Takara) in a 25 μl volume. Thermocycler settings were: 94° C., 1 minute followed by 30 cycles of 94° C., 20 seconds; 78° C., 30 seconds; 66° C., 12 minutes. PCR products (5 μl each) were separated on a 0.4% agarose gel also containing λ Hind III markers. See FIG. 6. The band for the amplicon with the deletion is clearly visible in lane 5. (Lane 6 contains a PCR artifact). Thus, the PNA probe suppressed amplification of the wild-type DNA samples, but the deletion was amplified, thereby identifying the plant tissue sample that had a deletion.

EXAMPLE 6

Use of "Poison Primer" to Detect Deletion Mutants in Pool of Mixed Plant DNA

This example indicates how the use of additional primers in PCR can enhance the detection of deletions in genes of interest. As in Example 5, primers for long PCR are designed to bind to DNA flanking the target gene so that a product, which includes the target gene and is up to 20 kb in length, is generated by long PCR from these opposing "outer" primers. A second pair of nested primers is also designed to bind to sequences just inside the outer primers. In a typical nested PCR procedure, a primary reaction is run using genomic DNA as the template and a set of outer primers for amplification. A small amount of the primary PCR product is then used as template in a secondary PCR that utilizes a set of nested primers for amplification. Because the majority of molecules that serve as templates for the nested primers in the secondary reaction are those produced from the pair of outer primers in the primary reaction, this two-stage process typically results in an abundant yield of the expected PCR product, with little or no non-specific PCR products being formed.

This example modifies the traditional two-stage nested PCR by adding at least one additional primer that binds between the two outer primers of the primary PCR. This "poison primer" is designed to hybridize to the target gene and, together with one of the outer primers, leads to the formation of a PCR "poison product" that is only about half the size of a product formed between the two outer primers with no poison primer therebetween. Due to the kinetic advantage (as discussed in Example 5), the shorter poison product will predominate in the primary PCR. When this primary product is used as a template in the secondary reaction, little or no full-length product is formed because a binding site for one of the two nested primers does not exist on the poison product. If however, a deletion removes the binding site for the poison primer (but not any binding sites for the nested or outer primers), the poison product can no longer form in the primary PCR. In the secondary PCR, both nested primers will bind to the primary template and lead to formation of a product that signals the presence of the deletion.

Figure 7:
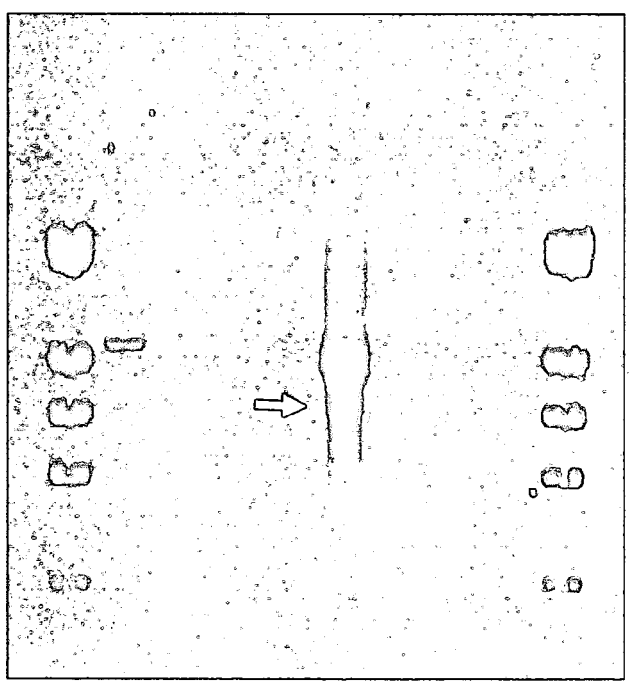
FIG. 7 shows an agarose gel exemplifying a poison primer method of the subject invention used to identifying a deletion in canola.

The "poison primer" method was used to detect a deletion in canola. These methods used the same eight samples as described in the preceding Example. Again, the eight samples, each containing approximately 15 ng of genomic DNA (pooled from samples representing 15 $M_2$ families sampled at the rate of approximately 5 seeds per family) were subjected to PCR using primers D199 (SEQ ID NO:5) and D200 (SEQ ID NO:6) plus the poison primer D249 (SEQ ID NO:8). Thermocycler settings were: 94° C., 1 minute followed by 30 cycles of 94° C., 20 seconds; 78° C., 30 seconds; 68° C., 12 minutes. The PCR products (1 III each) were separated on a 0.4% agarose gel also containing λ Hind III markers. See FIG. 7. The band for the amplicon with the deletion is indicated in lane 5. (The preferential amplification of the deletion worked so well that even less DNA could have been loaded into this well; this would have yielded a more distinct deletion band.) Some wild-type product is visible in lanes 1, 4, and 6-8. The wild-type product was suppressed in lanes 2 and 3 to the extent that no wild-type bands are visible in those two lanes. This illustrates that the band for the amplicons with the deletion (being smaller than the wild-type amplicons in some of the other lanes) are clearly identifiable and that amplification of wild-type DNA can be completely or sufficiently suppressed using this method of the subject invention.

EXAMPLE 7

Gene Mutation Scanning (GMS)

This example describes a screening method, with two variations, that can be used to detect deletions or other mutations (including point mutants) within pooled samples of DNA from multiple lines. These mutations (including deletions) must occur within a window defined by long-range PCR from primers flanking a target gene as in previous examples. In this method, the initial long PCR product is digested with one or more restriction enzymes. The resulting restriction fragments are then subjected to a second round of PCR using primers that would not support PCR amplification except in rare cases where a mutation or deletion event removed one or more of the recognition sites for the restriction enzyme(s) used in the previous step.

To be successful, the GMS method requires complete or nearly complete sequence information for the target gene (including introns) and all flanking DNA contained within the initial long PCR product. This information can be obtained, for example, by sequencing the insert from one or more large genomic clones (BAC, cosmid, etc) that contain the target gene and its flanking DNA. Such clones can be identified by screening libraries of these clones by standard methods that utilize the sequences derived from the target gene as a probe. Alternatively, the information can be obtained by fully sequencing many of the intermediate products obtained while chromosome walking from the two ends of the target gene, for example by the GenomeWalker™ method.

A collection of $M_2$ families, derived from a mutagenesis utilizing a deletion-inducing agent such as fast neutron radiation, is generated as in previous examples. Using the sequence information obtained by one of the above methods, primers that bind to regions flanking the target gene are designed for long PCR. In addition, one or more restriction enzymes are chosen to digest the initial PCR product into several fragments. Fragment lengths ranging from approximately 500 bp to 2000 bp are preferred, although this method can utilize restriction fragment lengths outside of that range. Finally, PCR primers that bind to the restriction fragments (RF primers) are designed. The position of these RF primers on the restriction fragments is determined by the choice of two possible variations of the method.

In the first variation, it is desired to identify deletions that remove one, or possibly two of the multiple restriction sites that occur within the initial long PCR product. For example a single targeted restriction site (TRS) within an exon of the target gene could be selected to identify deletions that remove some or all of the target gene. Such deletions would be expected to generate complete loss of function mutations. Alternatively, a TRS upstream and a TRS downstream of the target gene could be chosen to be screened simultaneously in order to identify deletions that occur in the flanking regions. A deletion of this type could potentially lead to a partial loss or gain of function in the target gene if it left the coding region and minimal regulatory elements intact but removed other regulatory elements, such as enhancers or suppressors, that may exist in the flanking DNA.

Figure 8:
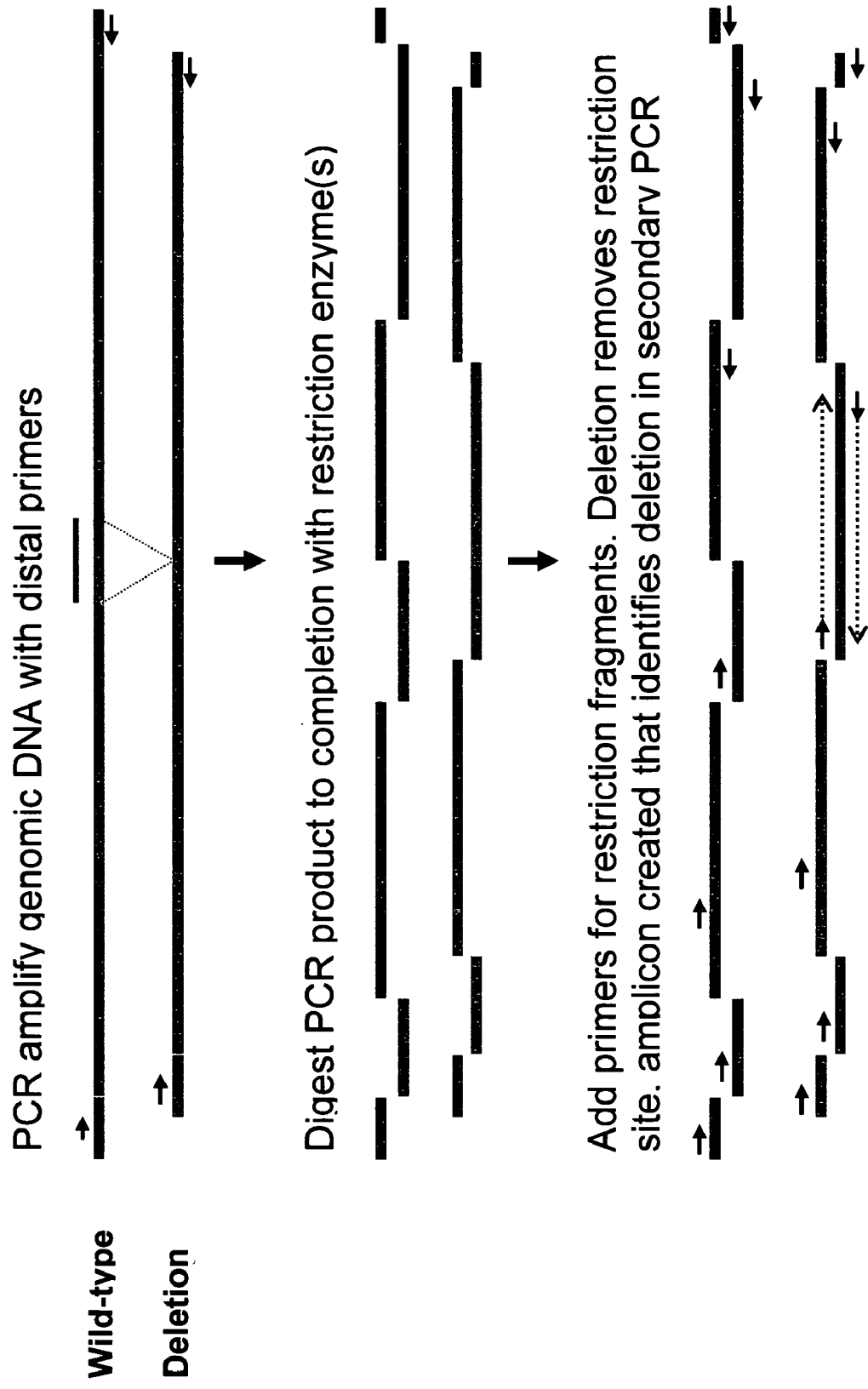
FIG. 8 shows a basic illustration of one type of Gene Mutation Scanning approach.

In the first variation, one RF primer is positioned on each restriction fragment as far from the TRS as possible. See FIG. 8. Sense RF primers are positioned near the upstream end of fragments upstream of the TRS, and antisense RF primers are positioned near the downstream end of fragments downstream of the TRS, so that a series of nested primers "pointing towards" the TRS is created. Under this arrangement, the initial long PCR product, fully digested by the selected enzyme(s), would not be a suitable template for the second round PCR using the RF primers. However, if a variant existed within the pooled DNA sample where a deletion had removed the TRS but not the binding sites for at least one sense and one antisense RF primer, then a PCR product could accumulate that would signal the presence of the deletion. In cases where more than one TRS is selected, the initial long PCR product would be divided into separate sub-section for each TRS. Within each sub-section, sense RF primers would be positioned near the upstream end of fragments upstream of the respective TRS and antisense RF primers would be positioned near the downstream end of the downstream fragments. In these cases, only deletions that removed the TRS and left intact at least one sense and one antisense RF primer binding site within the sub-section for the TRS would be detected.

In the second variation, it is desired to identify deletions that remove any one or more of the restriction enzyme recognition sites within the initial long PCR product. In this variation, most of the restriction fragments would have two RF primers designed to bind near their centers, with the sense primers positioned slightly downstream of the antisense primers. See FIG. 9. Under this arrangement the DNA polymerase could extend a product from the primers to the ends of the restriction fragments, but the products would not overlap and therefore exponential amplification of DNA would not be supported. However, in cases where a rare deletion event removed one or more restriction sites but left at least one sense and one antisense priming site intact, PCR would be supported.

Figure 9:
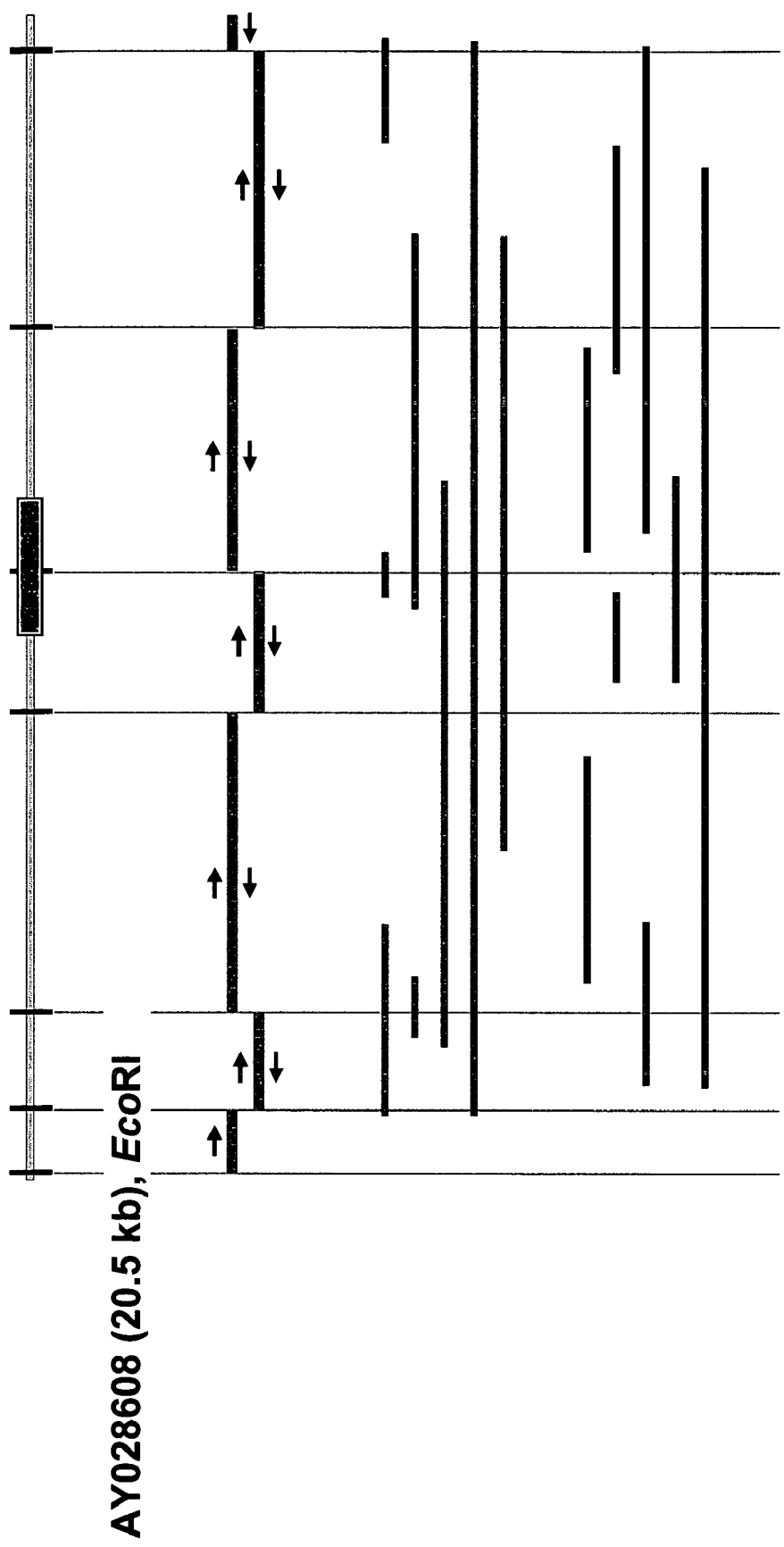
FIG. 9 shows a basic illustration of a variation of the Gene Mutation Scanning approach.
Figure 10:
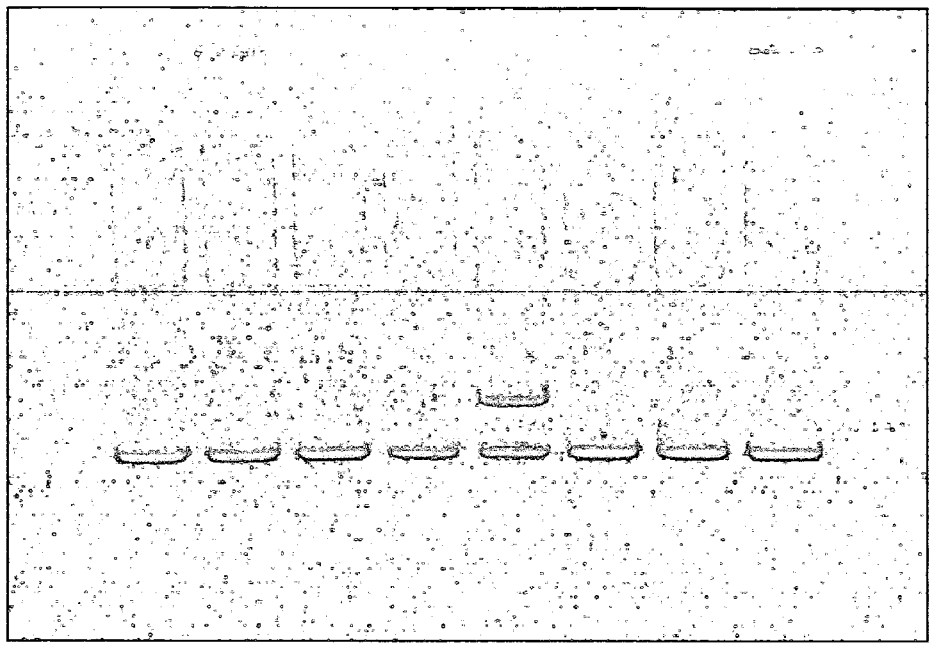
FIG. 10 shows an agarose gel exemplifying a GMS method of the subject invention used to identifying a deletion in canola. Genomic DNA was first amplified, and the resulting amplicon was then digested with a restriction enzyme.
Figure 11:
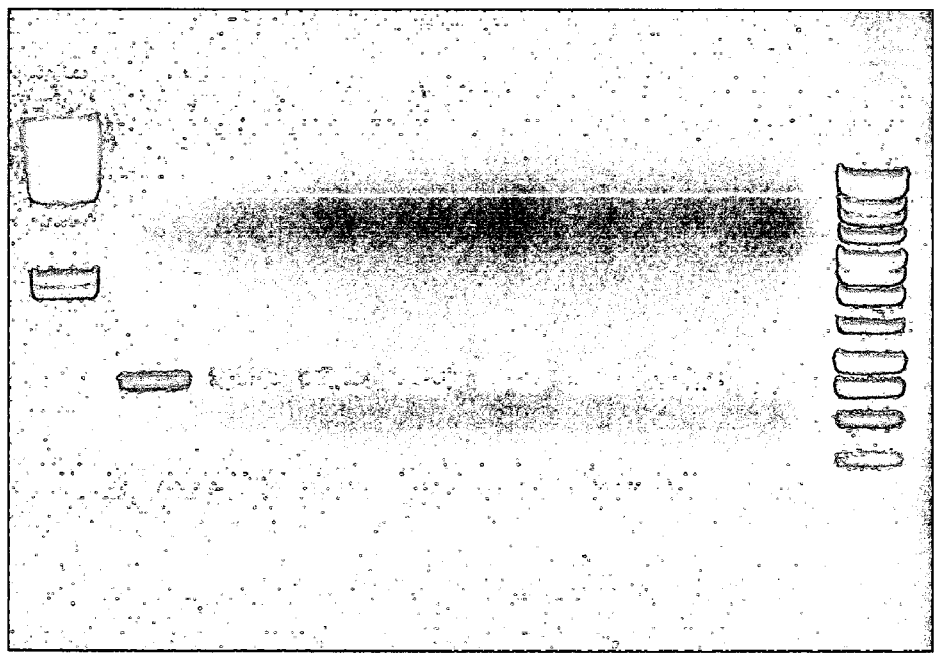
FIG. 11 shows an agarose gel exemplifying a GMS method of the subject invention used to identifying a deletion in canola. With the approach used to generate this gel, genomic DNA was digested with a restriction enzyme (without prior amplification as in the technique used to generate the gel of FIG. 10).
Figure 12:
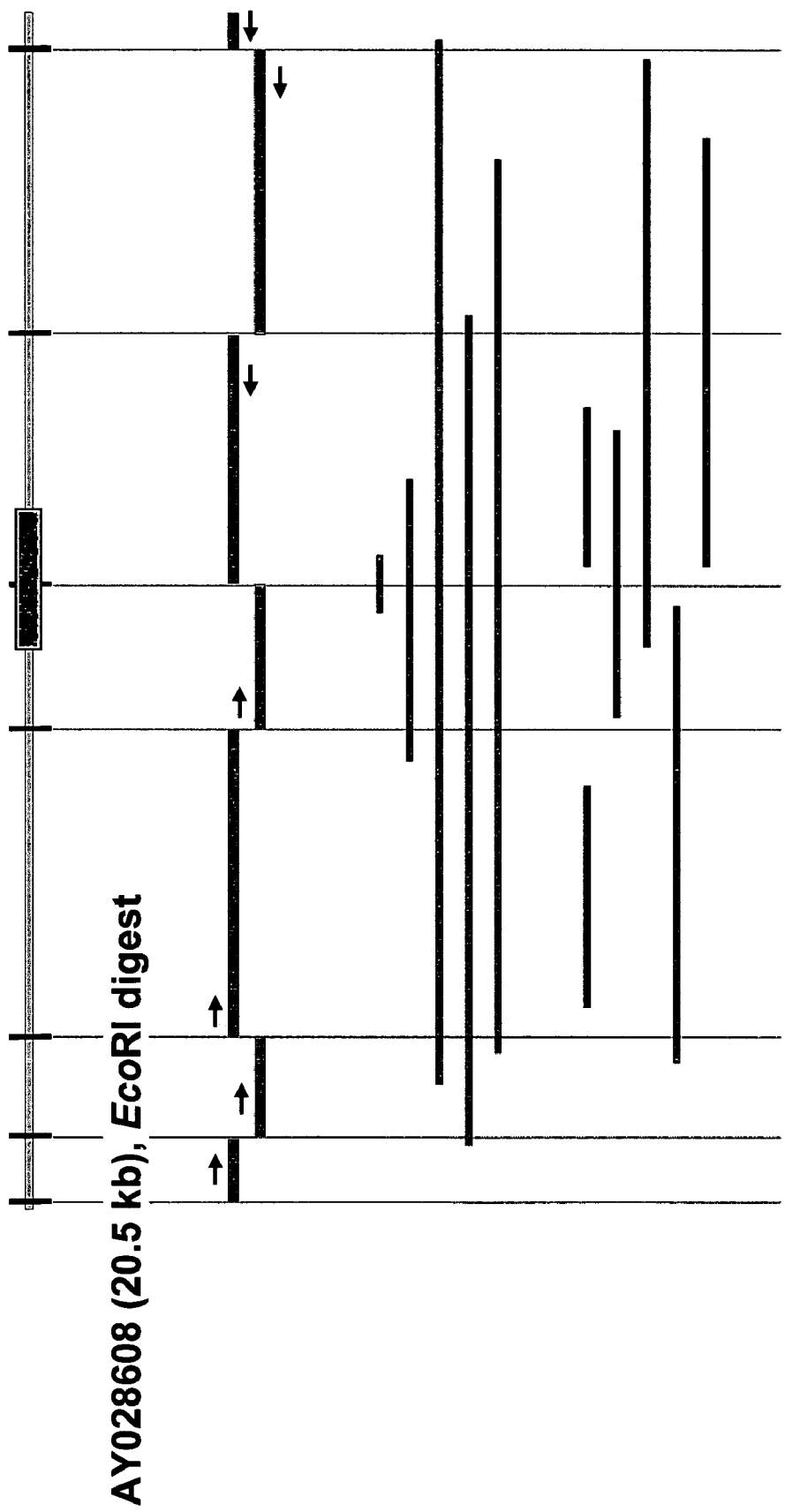
FIG. 12 illustrates the concept used to produce the results shown in FIG. 11.

Two approaches were used to exemplify the GMS methodology for detecting a deletion in canola. These methods were exemplified using the same known deletion and eight samples used in the PNA and poison primer Examples above. In the first approach (see FIG. 10), pooled Brassica napus genomic DNA (for wild-type lines and for the deletion line) was first amplified with two primers D199 (SEQ ID NO:5) and D200 (SEQ ID NO:6). The resulting PCR amplicon was digested with Nco I restriction enzyme. In the second approach (see FIG. 11), pooled Brassica napus genomic DNA was digested with Nco I restriction enzyme. For both approaches, the digested product was amplified with the following five primers (using Multiplex PCR): D195 (SEQ ID NO:11), D201 (SEQ ID NO:12), D209 (SEQ ID NO:13), D190 (SEQ ID NO:10), and D200 (SEQ ID NO:6). The PCR products were then resolved on 0.8% agarose gel. See FIGS. 10 and 11. In both figures, the amplicon resulting from the removal of a restriction site (the deletion) is apparent in lane 5. This shows that the removal of the restriction site resulted in proper alignment of the GMS primers of the subject invention, thereby resulting in amplification of DNA from a tissue sample having a deletion. The absence of this amplicon in the other lanes signifies that the wild-type restriction sites were maintained and, thus, amplification from the isolated GMS primers did not occur for the wild-type samples. The concept used to produce the results in FIG. 11 is illustrated in FIG. 12. The amplicons shown at the bottom of FIG. 12 illustrate non-detectable deletions which do not eliminate central restriction sites or primer sites. The amplicons above those illustrate detectable deletions which must eliminate central restriction sites but not outer primer sites. This is similar for what is illustrated in FIG. 9.

The invention claimed is:

1. A method of detecting mutant DNA wherein said method comprises the steps of:

a) providing at least one DNA sample derived from at least one tissue sample;

b) digesting said at least one DNA sample with at least one restriction enzyme to obtain a plurality of restriction fragments;

c) providing more than two upstream RF primers that bind upstream of a targeted restriction site on said DNA sample, and more than two downstream RF primers that bind downstream of said targeted restriction site on said DNA sample, said primers binding in orientations that permit generation of an amplicon between any said upstream RF primer and any said downstream RF primer only when a mutation is present in said DNA sample that removes a restriction site in said DNA sample, and wherein said amplicon is not produced in the absence of a mutation;

d) subjecting said restriction fragments and said RF primers to PCR amplification conditions to obtain a PCR sample; and e) assaying said PCR sample for the presence of said amplicon that indicates the presence of said mutation that removed the restriction site from said DNA sample.

2. A method of detecting mutant DNA wherein said method comprises the steps of:

a) providing at least one DNA sample derived from at least one tissue sample;

b) digesting said at least one DNA sample with at least one restriction enzyme to obtain a plurality of restriction fragments;

c) providing more than two RF sense primers and more than two antisense RF primers, each said RF primers being designed to hybridize to at least one of said restriction fragments, wherein a first sense RF primer and a first antisense RF primer are designed to bind to a first restriction fragment and to produce an amplicon with a second antisense RF primer or a second sense RF primer only in the presence of a mutation that removes a restriction site, wherein said second antisense RF primer and said second sense RF primer are designed to bind to a second restriction fragment in the absence of said mutation, wherein one of said sense RF primers and one of said antisense RF primers facilitate production of said amplicon only when said mutation is present in said DNA sample that removes a restriction site in said DNA sample in which case said first sense RF primer, said first antisense RF primer, said second sense RF primer, and said second antisense RF primer bind to the same restriction fragment, and wherein said amplicon is not produced in the absence of a mutation;
  d) subjecting said restriction fragments and said RF primers to PCR amplification conditions to obtain a PCR sample; and
  e) assaying said PCR sample for the presence of said amplicon that indicates the presence of said mutation that removed the restriction site from said DNA sample.

3. The method of claim 1 wherein said restriction fragments are approximately 500 to 2000 basepairs in length.

4. The method according to claim 1 wherein said tissue sample is plant tissue.

5. A method of detecting mutant DNA wherein said method comprises the steps of:
  a) providing at least one DNA sample derived from at least one tissue sample, wherein said DNA sample is obtained from plant cells descendant from said tissue sample;
  b) digesting said at least one DNA sample with at least one restriction enzyme to obtain a plurality of restriction fragments;
  c) providing a plurality of upstream RF primers that bind upstream of a targeted restriction site on said DNA sample, and a plurality of downstream RF primers that bind downstream of said targeted restriction site on said DNA sample, said primers binding in orientations that permit generation of an amplicon between any said upstream RF primer and any said downstream RF primer only when a mutation is present in said DNA sample that removes a restriction site in said DNA sample, and wherein said amplicon is not produced in the absence of a mutation;
  d) subjecting said restriction fragments and said RF primers to PCR amplification conditions to obtain a PCR sample; and
  e) assaying said PCR sample for the presence of said amplicon that indicates the presence of said mutation that removed the restriction site from said DNA sample.

6. The method according to claim 5 wherein said plant cells are obtained from a source selected from the group consisting of M1 seed, M2 seed, M3 seed, M4 seed, M5 seed, M6 seed, an M1 plant, an M2 plant, an M3 plant, an M4 plant, an M5 plant, and an M6 plant.

7. The method according to claim 6 wherein said DNA sample is obtained from a plant grown from an M3 seed and said M3 seed was produced by a plant grown from an M2 seed that was produced by a plant grown from M1 seed that was subjected to mutagenesis.

8. A method of detecting mutant DNA wherein said method comprises the steps of:
  a) providing at least one DNA sample derived from at least one tissue sample, wherein said DNA sample is obtained from a progeny plant related to a source plant of said tissue sample;
  b) digesting said at least one DNA sample with at least one restriction enzyme to obtain a plurality of restriction fragments;
  c) providing a plurality of sense and antisense RF primers, each said RF primers being designed to hybridize to at least one of said restriction fragments, wherein a first sense RF primer and a first antisense RF primer are designed to bind to a first restriction fragment and to produce an amplicon with a second antisense RF primer or a second sense RF primer only in the presence of a mutation that removes a restriction site, wherein said second antisense RF primer and said second sense RF primer are designed to bind to a second restriction fragment in the absence of said mutation, wherein one of said sense RF primers and one of said antisense RF primers facilitate production of an amplicon only when a mutation is present in said DNA sample that removes a restriction site in said DNA sample in which case said first sense RF primer, said first antisense RF primer, said second sense RF primer, and said second antisense RF primer bind to the same restriction fragment, and wherein said amplicon is not produced in the absence of a mutation;
  d) subjecting said restriction fragments and said RF primers to PCR amplification conditions to obtain a PCR sample; and
  e) assaying said PCR sample for the presence of said amplicon that indicates the presence of said mutation that removed the restriction site from said DNA sample.

9. The method according to claim 1 wherein said DNA sample is pooled with a plurality of other DNA samples to form a DNA pool after the step of obtaining said DNA sample and prior to the steps of providing said primers.

10. The method according to claim 1 wherein said assaying step is conducted using a technique selected from the group consisting of gel electrophoresis and plate-based fluorescent assay.

11. A method of detecting mutant DNA wherein said method comprises the steps of:
  a) providing at least one DNA sample derived from at least one tissue sample;
  b) digesting said at least one DNA sample with at least one restriction enzyme to obtain a plurality of restriction fragments;
  c) providing a plurality of sense and antisense RF primers, each said RF primers being designed to hybridize to at least one of said restriction fragments, wherein a first sense RF primer and a first antisense RF primer are designed to bind to a first restriction fragment and to produce an amplicon with a second antisense RF primer or a second sense RF primer only in the presence of a mutation that removes a restriction site, wherein said second antisense RF primer and said second sense RF primer are designed to bind to a second restriction fragment in the absence of said mutation, wherein one of said sense RF primers and one of said antisense RF primers facilitate production of an amplicon only when a mutation is present in said DNA sample that removes a restriction site in said DNA sample in which case said first sense RF primer, said first antisense RF primer, said second sense RF primer, and said second antisense RF primer bind to the same restriction fragment, and wherein said amplicon is not produced in the absence of a mutation;
  d) subjecting said restriction fragments and said RF primers to PCR amplification conditions to obtain a PCR sample;
  e) performing a second PCR step that amplifies said amplicon produced in the presence of said mutation that removes a binding site of a third primer; and
  f) assaying said PCR sample, after said second PCR step, for the presence of said amplicon that indicates the presence of said mutation that removed the restriction site from said DNA sample.

12. The method of claim 1 wherein a first PCR step is performed prior to said digesting step in order to form primary amplicons from genomic DNA, and said digesting step is performed on said primary amplicons.

13. The method according to claim 1 wherein said tissue sample was subjected to mutagenesis.

14. The method according to claim 13 wherein said mutagenesis is selected from the group consisting of radiation-based mutagenesis and chemical mutagenesis.

15. The method according to claim 14 wherein said mutagenesis is radiation-based mutagenesis and said radiation-based mutagenesis is fast neutron mutagenesis.

16. The method according to claim 14 wherein said mutagenesis is chemical mutagenesis and said chemical mutagenesis is selected from the group consisting of diepoxybutane (DEB), diepoxyoctane (DEO), ethyl methanesulfonate (EMS), N-ethyl-N-nitrosourea (ENU), N-methyl-N nitrosourea (MNU), and methylmethane sulfonate (MMS).

17. The method according to claim 1 wherein said mutation is a deletion.

18. A method of detecting mutant DNA wherein said method comprises the steps of:
  a) providing at least one DNA sample derived from at least one tissue sample; wherein said tissue sample is pollen and said DNA sample is obtained from a plant that is pollinated with said pollen that was subjected to mutagenesis;
  b) digesting said at least one DNA sample with at least one restriction enzyme to obtain a plurality of restriction fragments;
  c) providing a plurality of upstream RF primers that bind upstream of a targeted restriction site on said DNA sample, and a plurality of downstream RF primers that bind downstream of said targeted restriction site on said DNA sample, said primers binding in orientations that permit generation of an amplicon between any said upstream RF primer and any said downstream RF primer only when a mutation is present in said DNA sample that removes a restriction site in said DNA sample, and wherein said amplicon is not produced in the absence of a mutation;
  d) subjecting said restriction fragments and said RF primers to PCR amplification conditions to obtain a PCR sample; and
  e) assaying said PCR sample for the presence of said amplicon that indicates the presence of said mutation that removed the restriction site from said DNA sample.

19. The method of claim 2 wherein said hybridization conditions are adjusted to allow for partial blockage of PCR amplification in the presence of some bound PNA probe so as to provide a positive control indicating that the PCR amplification is properly proceeding.

20. The method of claim 2 wherein said hybridization and amplification steps are conducted under conditions that prevent essentially all amplification of wild-type DNA in the presence of bound PNA probe.

21. The method of claim 1 wherein said restriction fragment has a 5' end and a 3' end, and one said RF primer is designed to bind to each restriction fragment near the 5' or 3' end of said restriction fragment.

22. The method of claim 1 wherein a first RF primer and a second RF primer are designed to bind to each restriction fragment, and wherein said first RF primer and said second RF primer are designed to initiate amplification in opposite directions.

23. The method of claim 1 wherein said mutation is a point mutation.

24. The method of claim 2 wherein said mutation is a deletion.

25. The method of claim 3 wherein said mutation is a deletion.

26. The method of claim 2 wherein said mutation is a point mutation.

27. The method of claim 3 wherein said mutation is a point mutation.

28. The method of claim 4 wherein said plant tissue is tissue from a plant selected from the group consisting of canola, corn, *Arabidopsis*, cotton, sunflower, soybean, wheat, barley, sorghum, rice, tomato, and castorbean.

29. The method according to claim 3 wherein said DNA sample is obtained from plant cells descendant from said tissue sample.

30. The method according to claim 2 wherein said DNA sample is pooled with a plurality of other DNA samples to form a DNA pool after the step of obtaining said DNA sample and prior to the steps of providing said primers.

31. The method according to claim 3 wherein said DNA sample is pooled with a plurality of other DNA samples to form a DNA pool after the step of obtaining said DNA sample and prior to the steps of providing said primers.

* * * * *

UNITED STATES PATENT AND TRADEMARK OFFICE
CERTIFICATE OF CORRECTION

PATENT NO.         : 7,354,715 B2
APPLICATION NO. : 10/851924
DATED                  : April 8, 2008
INVENTOR(S)       : Avutu Sambi Reddy et al.

It is certified that error appears in the above-identified patent and that said Letters Patent is hereby corrected as shown below:

Column 3,
Line 58, "TMP[UV" should read --TMP/UV--.
Line 63, "TMP[UV" should read --TMP/UV--.

Column 5,
Line 43, "PCR screening. [0023] FIG. 2 shows PCR products" should read
            --PCR screening.
                 FIG. 2 shows PCR products--.

Column 15,
Line 30, "9–2" should read --96 – 2--.

Column 17,
Line 10, "9.5 µ3 M" should read --9.5 µl 3 M--.

Column 21,
Line 31, "(1 III)" should read --(1 µl)--.

Signed and Sealed this

Fourteenth Day of October, 2008

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 34
<212> TYPE: DNA
<213> ORGANISM: Artificial Sequence
<220> FEATURE:
<223> OTHER INFORMATION: Primer used according to the subject invention

<400> SEQUENCE: 1
gaattatcta ctatgtgagc tatttgttcc tgag                                34

<210> SEQ ID NO 2
<211> LENGTH: 34
<212> TYPE: DNA
<213> ORGANISM: Artificial Sequence
<220> FEATURE:
<223> OTHER INFORMATION: Primer used according to the subject invention

<400> SEQUENCE: 2
ccttcatcta atcagaacat gtaagtagaa tgtg                                34

<210> SEQ ID NO 3
<211> LENGTH: 18
<212> TYPE: DNA
<213> ORGANISM: Artificial Sequence
<220> FEATURE:
<223> OTHER INFORMATION: PNA probe used according to the subject
      invention

<400> SEQUENCE: 3
caaactgaac caaacccg                                                  18

<210> SEQ ID NO 4
<211> LENGTH: 18
<212> TYPE: DNA
<213> ORGANISM: Artificial Sequence
<220> FEATURE:
<223> OTHER INFORMATION: PNA probe used according to the subject
      invention
```

```
<400> SEQUENCE: 4
tggtttcggt atgatcca                                                 18

<210> SEQ ID NO 5
<211> LENGTH: 30
<212> TYPE: DNA
<213> ORGANISM: Artificial Sequence
<220> FEATURE:
<223> OTHER INFORMATION: Primer D199 (sense primer, aligns at
      approximately residue [2,101-] of GENBANK Accession No. AJ245480).

<400> SEQUENCE: 5
acgtcctcct caacctcgtt aagacacttg                                    30

<210> SEQ ID NO 6
<211> LENGTH: 31
<212> TYPE: DNA
<213> ORGANISM: Artificial Sequence
<220> FEATURE:
<223> OTHER INFORMATION: primer D200 (antisense primer, aligns at
      approximately residue [-19,162] of GENBANK Accession No.
      AJ245480).

<400> SEQUENCE: 6
cttcttcatc agcttgctaa ggaggggtaa g                                  31

<210> SEQ ID NO 7
<211> LENGTH: 18
<212> TYPE: DNA
<213> ORGANISM: Artificial Sequence
<220> FEATURE:
<223> OTHER INFORMATION: PNA probe Q108.

<400> SEQUENCE: 7
aggtgcagcc agctacat                                                 18

<210> SEQ ID NO 8
<211> LENGTH: 30
<212> TYPE: DNA
<213> ORGANISM: Artificial Sequence
<220> FEATURE:
<223> OTHER INFORMATION: Primer D249 (sense primer for poison primer
      test, aligns at approximately residue [14,828-] of GENBANK
      Accession No. AJ245480).

<400> SEQUENCE: 8
gtttgtagag atgtcaactg ggtgggcagt                                    30

<210> SEQ ID NO 9
<211> LENGTH: 30
<212> TYPE: DNA
<213> ORGANISM: Artificial Sequence
<220> FEATURE:
<223> OTHER INFORMATION: Primer D245 (sense primer, aligns at
      approximately residue [2,243-] of GENBANK Accession No. AJ245480).

<400> SEQUENCE: 9
gaatagagct gatgggtcac tgacaaggag                                    30

<210> SEQ ID NO 10
<211> LENGTH: 30
<212> TYPE: DNA
<213> ORGANISM: Artificial Sequence
<220> FEATURE:
<223> OTHER INFORMATION: Primer D190 (Sense primer, aligns at
      approximately residue [-16,230] of GENBANK Accession No.
      AJ245480).
```

```
<400> SEQUENCE: 10
cactgtctgc ttaggactag ctgcatccat                                    30

<210> SEQ ID NO 11
<211> LENGTH: 30
<212> TYPE: DNA
<213> ORGANISM: Artificial Sequence
<220> FEATURE:
<223> OTHER INFORMATION: Primer D195 (Sense primer, aligns at
      approximately residue [11,851-] of GENBANK Accession No.
      AJ245480).

<400> SEQUENCE: 11
tggcctaggc catgtataac attaaaacag                                    30

<210> SEQ ID NO 12
<211> LENGTH: 32
<212> TYPE: DNA
<213> ORGANISM: Artificial Sequence
<220> FEATURE:
<223> OTHER INFORMATION: Primer D201 (Sense primer, aligns at
      approximately residue [12,650-] of GENBANK Accession No.
      AJ245480).

<400> SEQUENCE: 12
cggagaacaa gttatatgcc cattatgaca ct                                 32

<210> SEQ ID NO 13
<211> LENGTH: 30
<212> TYPE: DNA
<213> ORGANISM: Artificial Sequence
<220> FEATURE:
<223> OTHER INFORMATION: Primer D209 (Sense primer, aligns at
      approximately residue [15,443-] of GENBANK Accession No.
      AJ245480).

<400> SEQUENCE: 13
gcaccttctg tgctacaaca actaatcttt                                    30
```